United States Patent
Yokoyama et al.

(10) Patent No.: US 10,533,960 B2
(45) Date of Patent: Jan. 14, 2020

(54) METHOD FOR MANUFACTURING HIGH ASPECT RATIO STRUCTURE, A METHOD FOR MANUFACTURING ULTRASONIC PROBE, HIGH ASPECT RATIO STRUCTURE, AND X-RAY IMAGING APPARATUS

(71) Applicant: Konica Minolta, Inc., Tokyo (JP)

(72) Inventors: Mitsuru Yokoyama, Takatsuki (JP); Yuko Yamamoto, Takatsuki (JP)

(73) Assignee: KONICA MINOLTA, INC., Tokyo (JP)

( * ) Notice: Subject to any disclaimer, the term of this patent is extended or adjusted under 35 U.S.C. 154(b) by 212 days.

(21) Appl. No.: 15/908,107

(22) Filed: Feb. 28, 2018

(65) Prior Publication Data

US 2018/0259463 A1    Sep. 13, 2018

(30) Foreign Application Priority Data

Mar. 10, 2017   (JP) ................................. 2017-046372

(51) Int. Cl.

| | |
|---|---|
| *G01N 23/20* | (2018.01) |
| *B06B 1/06* | (2006.01) |
| *G01N 23/04* | (2018.01) |
| *G01N 29/24* | (2006.01) |
| *G01N 29/26* | (2006.01) |
| *G01N 23/083* | (2018.01) |

(52) U.S. Cl.
CPC ..... *G01N 23/20075* (2013.01); *B06B 1/0607* (2013.01); *B06B 1/0662* (2013.01); *G01N 23/04* (2013.01); *G01N 29/2437* (2013.01); *G01N 29/262* (2013.01); *G01N 23/083* (2013.01); *G21K 2207/005* (2013.01)

(58) Field of Classification Search
None
See application file for complete search history.

(56) References Cited

U.S. PATENT DOCUMENTS

| | | | | |
|---|---|---|---|---|
| 2015/0162402 | A1* | 6/2015 | Yasuzato | H01L 29/06 257/618 |
| 2016/0163408 | A1* | 6/2016 | Wang | B81C 1/00619 378/36 |
| 2016/0293284 | A1* | 10/2016 | Yokoyama | G01N 23/20008 |
| 2018/0138044 | A1* | 5/2018 | Mayer | H01L 21/2885 |

FOREIGN PATENT DOCUMENTS

JP      2017032476 A     2/2017

* cited by examiner

*Primary Examiner* — Hoon K Song
(74) *Attorney, Agent, or Firm* — Lucas & Mercanti, LLP

(57) ABSTRACT

In respective methods for manufacturing a high aspect ratio structure and an ultrasonic probe, a plurality of holes extending in a direction crossing a main surface of a substrate are formed, a plurality of first regions and second regions excluding the first regions from the main surface are periodically defined, and partition walls between the plurality of holes formed in the substrate corresponding to the first regions are removed by etching so that part of each of the partition walls within a predetermined range excluding a bottom portion is left. A high aspect ratio structure and an X-ray imaging apparatus include, over a side wall, a porous member including a plurality of holes extending in a direction crossing a grating surface within a predetermined range excluding a bottom portion in each of a plurality of recesses in a grating.

17 Claims, 31 Drawing Sheets

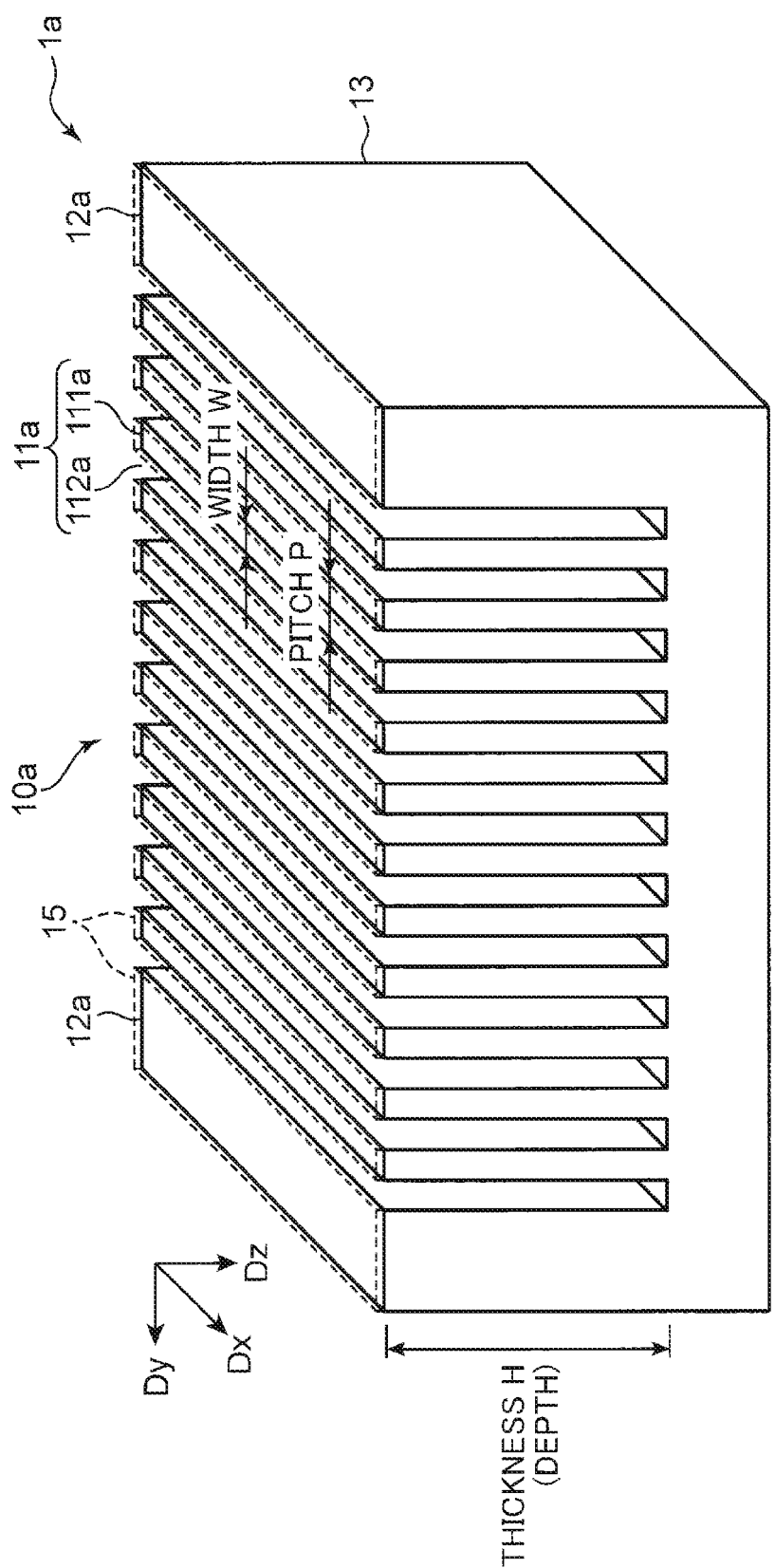

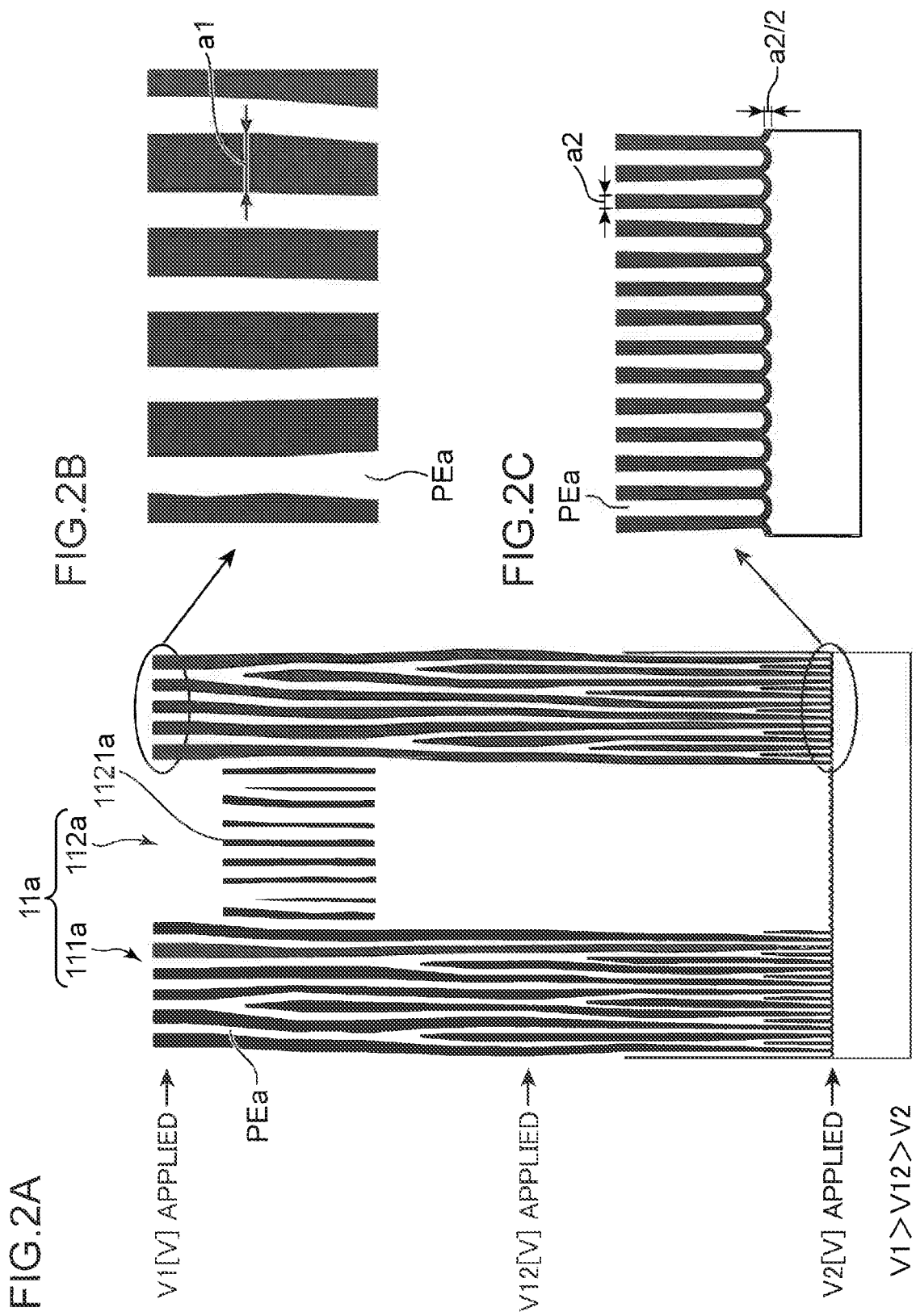

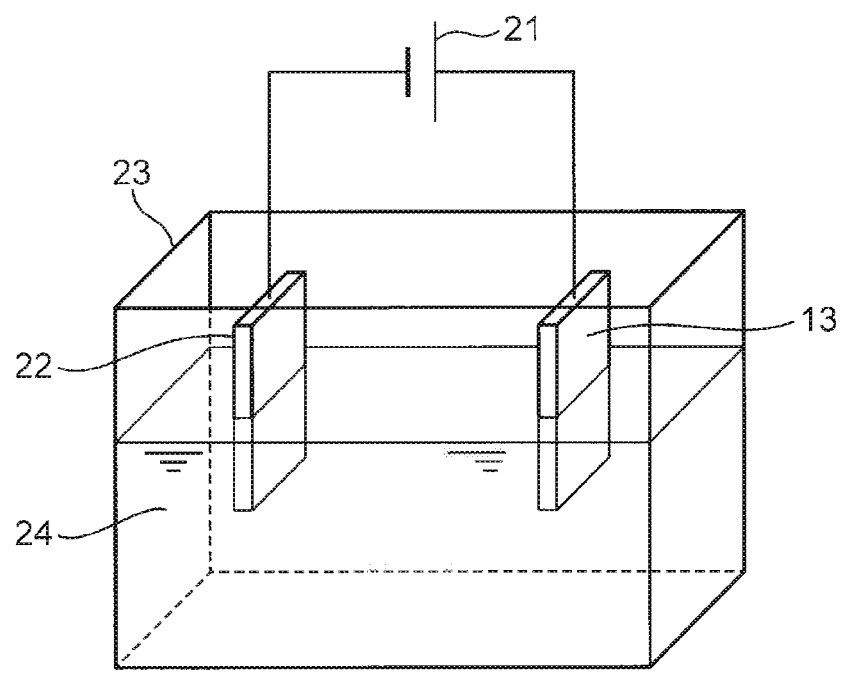

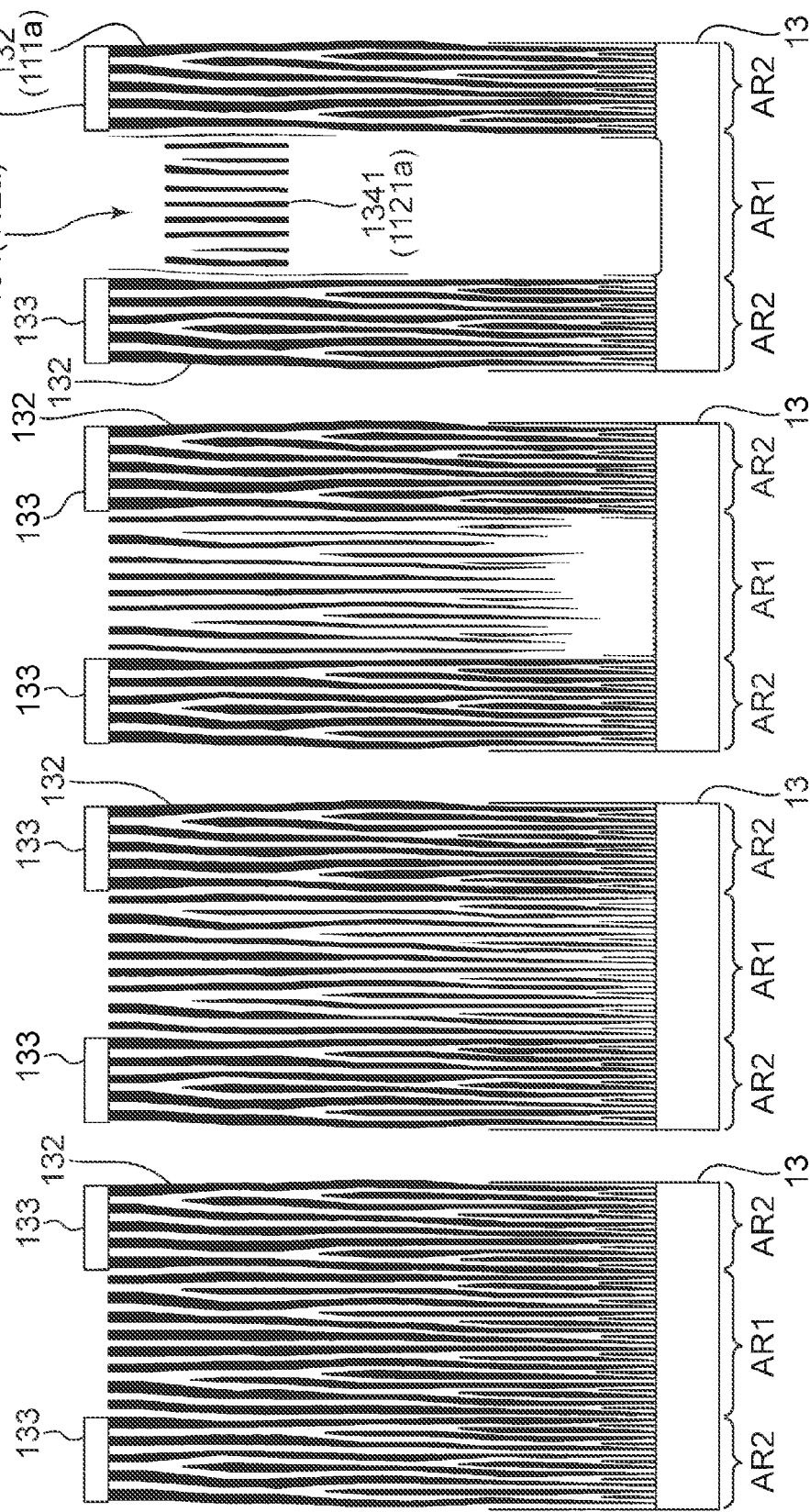

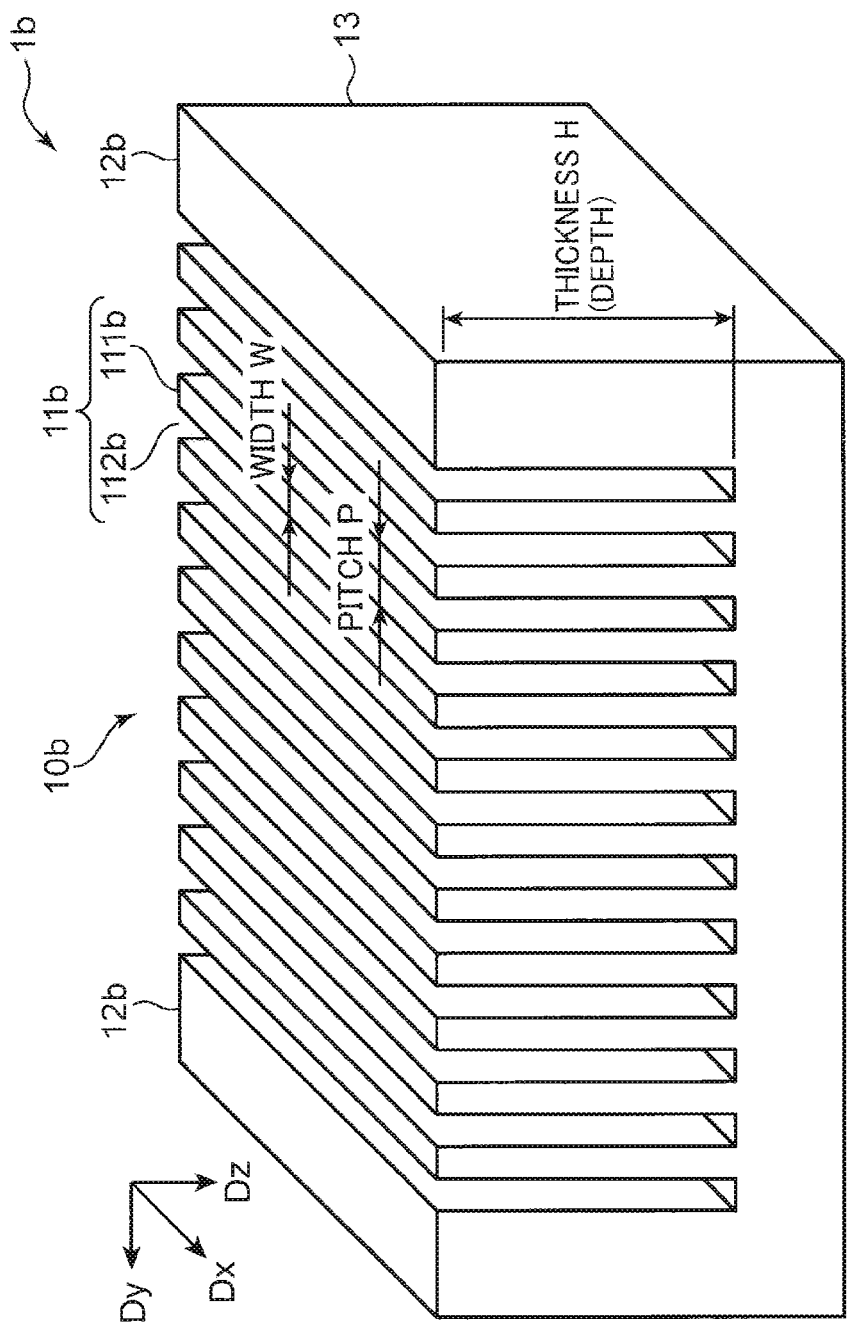

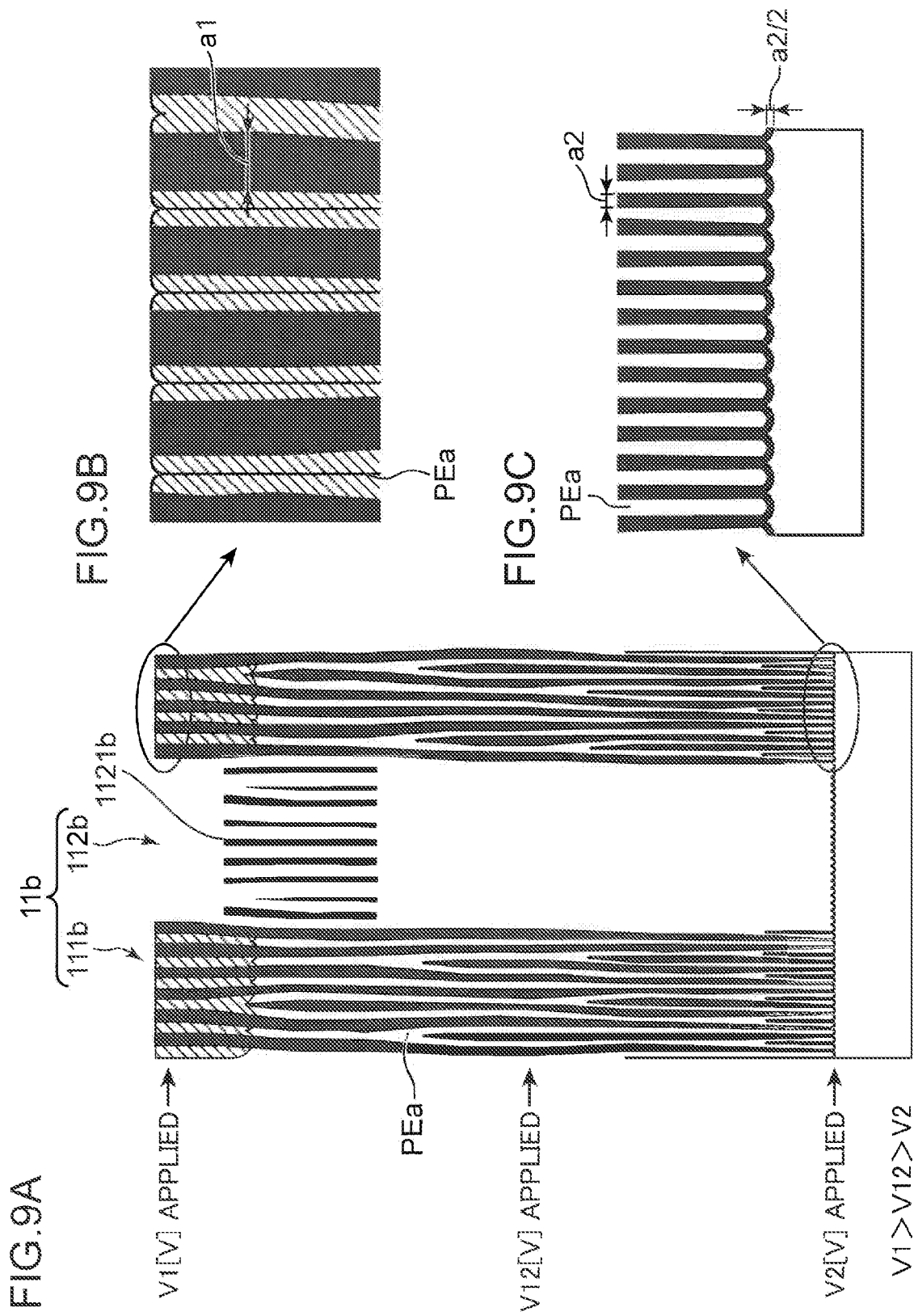

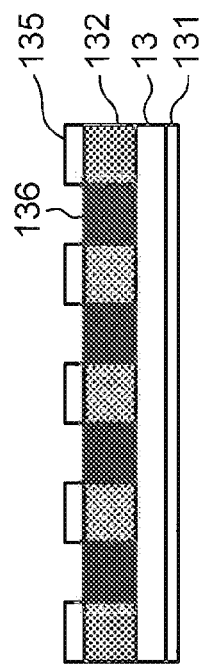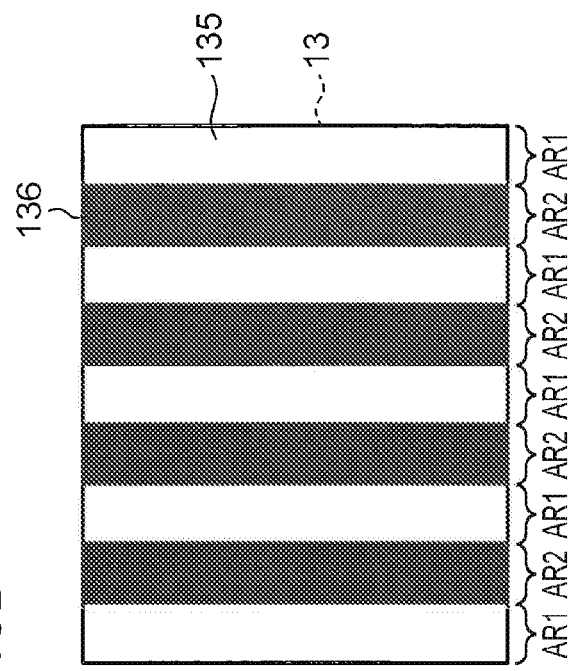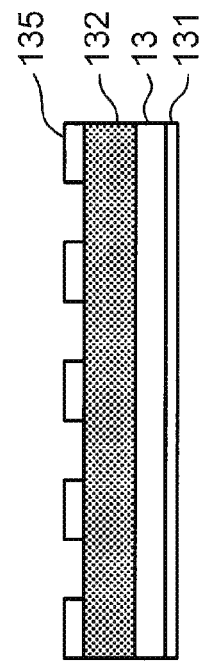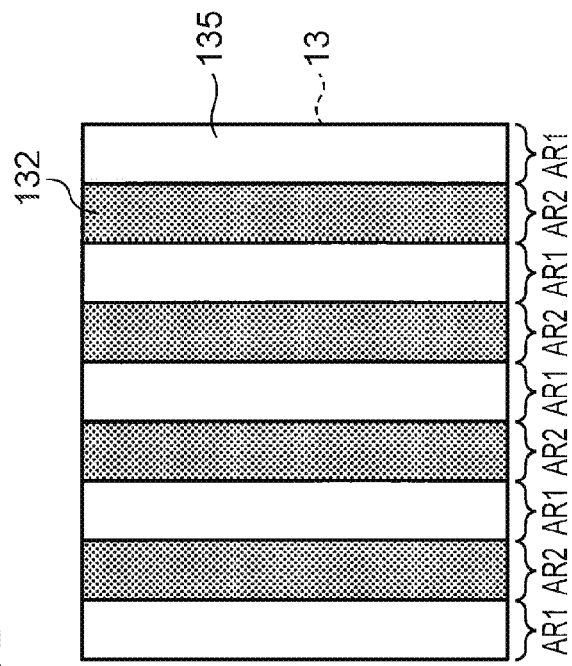

: BEFORE HOLE-SEALING TREATMENT

: AFTER HOLE-SEALING TREATMENT

: AFTER HOLE-SEALING TREATMENT

: AFTER HOLE-SEALING TREATMENT

: AFTER HOLE-SEALING TREATMENT

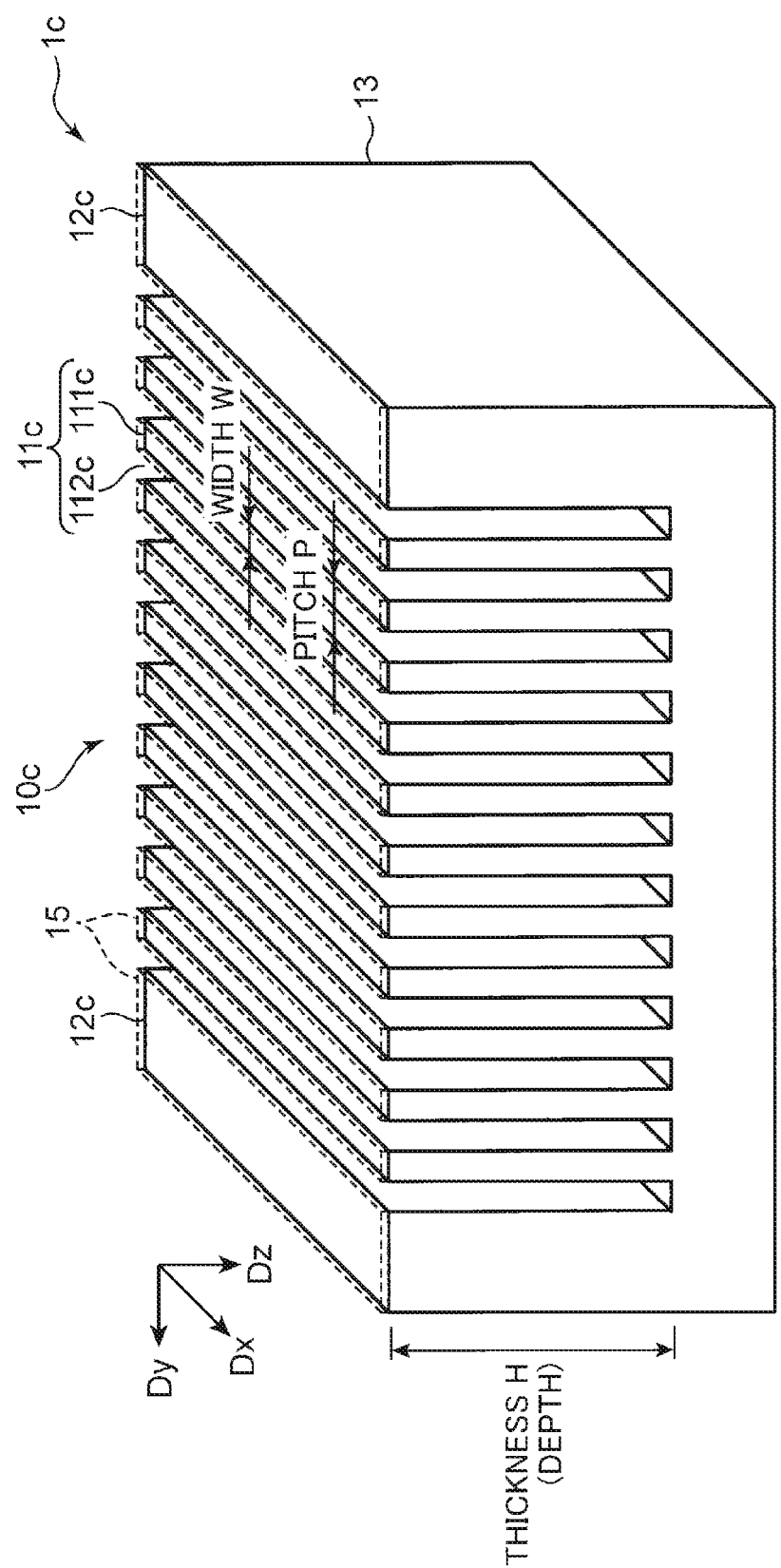

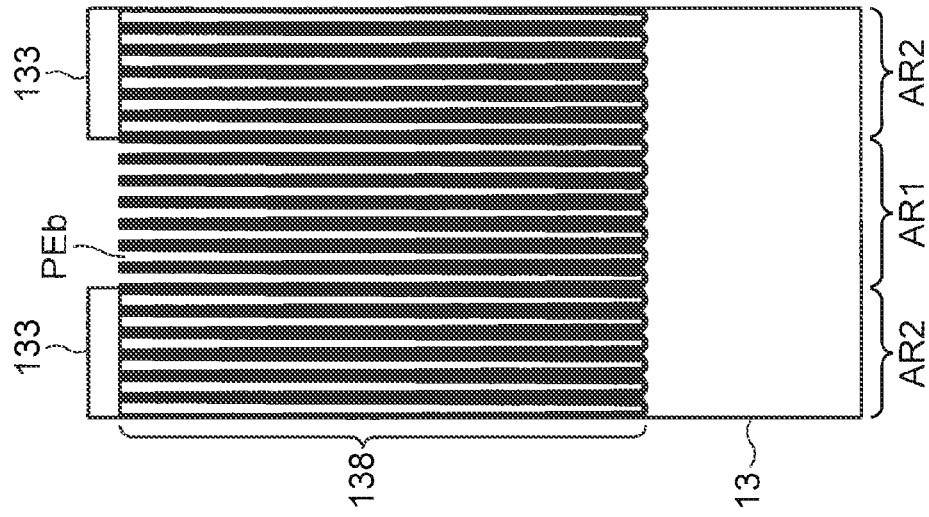
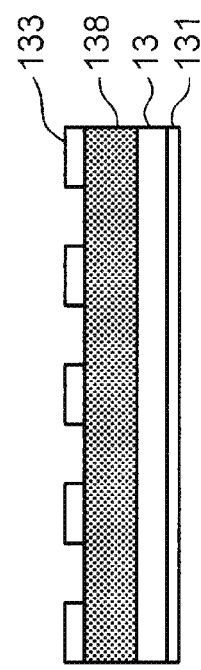
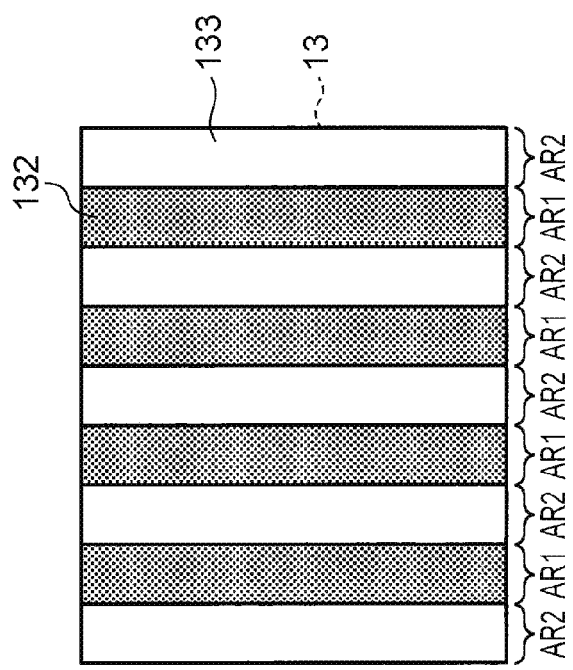

METHOD FOR MANUFACTURING HIGH ASPECT RATIO STRUCTURE, A METHOD FOR MANUFACTURING ULTRASONIC PROBE, HIGH ASPECT RATIO STRUCTURE, AND X-RAY IMAGING APPARATUS

TECHNOLOGICAL FIELD

The present invention relates to a method for manufacturing a high aspect ratio structure in which a structure of a high aspect ratio such as, for example, a metal grating for X-ray, an ultrasonic probe and the like having an aspect ratio of 3 or more is manufactured. The present invention relates to a method for manufacturing an ultrasonic probe in which an ultrasonic probe is manufactured using this method for manufacturing the high aspect ratio structure. The present invention relates to the above-described structure of a high aspect ratio and an X-ray imaging apparatus using the same.

BACKGROUND

For example, a metal grating for X-ray receiving X-rays is utilized in various apparatuses as an element including a number of parallel periodic structures, and in recent years, application to an X-ray imaging apparatus has been attempted. In this X-ray imaging apparatus, in recent years, X-ray phase imaging has been attracting attention in view of reduction in an exposure amount, for example, a Talbot interferometer or a Talbot-Lau interferometer has been applied. In this X-ray imaging apparatus including the Talbot-Lau interferometer, three metal gratings for X-ray of a 0-th grating, a first grating, and a second grating are used. This 0-th grating is a normal grating utilized to change a single X-ray source to a multi-light source, and divides an X-ray radiated from the single X-ray source into a plurality of X-rays (a plurality of X-ray beams) to radiate the same. These first and second gratings are diffraction grating disposed apart from each other by a Talbot distance to configure a Talbot-Lau interferometer (or Talbot interferometer). In this diffraction grating, when classified in a diffraction method, generally, there are a transmission type diffraction grating and a reflection type diffraction grating, and further, in the transmission type diffraction grating, an amplitude type diffraction grating (an absorption type diffraction grating) in which portions absorbing light are periodically arrayed on a substrate transmitting the light, and a phase type diffraction grating in which portions changing a phase of the light are periodically arrayed on a substrate transmitting the light.

The above-described X-ray phase imaging requires the absorption type diffraction grating, in which contrast between the portions transmitting X-rays and the portions not transmitting X-rays is distinct, and the phase type diffraction grating, in which a phase difference is distinct. Therefore, a grating of a high aspect ratio structure, which has a very high aspect ratio, for example, 3 or more is required. Therefore, a production method of applying a processing technique of a semiconductor has been proposed, and for example, in Japanese Unexamined Patent Application Publication No. 2017-32476, a method for manufacturing a high aspect ratio structure has been disclosed. The method for manufacturing the high aspect ratio structure disclosed in Japanese Unexamined Patent Application Publication No. 2017-32476 includes a hole formation step of forming a plurality of holes in at least one main surface of a substrate, a resist formation step of forming first regions where a resist layer is provided, and second regions where the resist layer is not provided in the main surface where the plurality of holes are formed after the hole formation step, and a recess formation step of forming recesses in the substrate corresponding to the second regions by immersing the substrate in an etching liquid.

Moreover, the above-described high aspect ratio structure can also be found in an ultrasonic probe.

In the method for manufacturing the high aspect ratio structure disclosed in Japanese Unexamined Patent Application Publication No. 2017-32476, a wet etching method is used. In this wet etching method, in a drying step of drying a workpiece after subjecting the workpiece to the wet etching, a phenomenon of sticking that the structure sticks attributed to a surface tension of the etching liquid may occur. Particularly, since the high aspect ratio structure has projections having a high aspect ratio, the sticking more easily occurs in the projections.

SUMMARY

The present invention is achieved in light of the above-described situation, an object thereof is to provide a method for manufacturing a high aspect ratio structure, in which the high aspect ratio structure is manufactured so that occurrence of sticking can be reduced more, and a method for manufacturing an ultrasonic probe, in which the ultrasonic probe using the high aspect ratio structure is manufactured. Another object of the present invention is to provide the above-described high aspect ratio structure, and an X-ray imaging apparatus using the same.

In order to realize the foregoing object, in respective methods for manufacturing a high aspect ratio structure and an ultrasonic probe on which one aspect of the present invention is reflected, a plurality of holes extending in a direction crossing a main surface of a substrate are formed, a plurality of first regions and second regions excluding the first regions from the main surface are periodically defined, and partition walls between the plurality of holes formed in the substrate corresponding to the first regions are removed by etching so that part of each of the partition walls within a predetermined range excluding a bottom portion is left. A high aspect ratio structure and an X-ray imaging apparatus on which one aspect of the present invention is reflected each include, over a side wall, a porous member including a plurality of holes extending in a direction crossing a grating surface within a predetermined range excluding a bottom portion in each of a plurality of recesses in a grating.

The advantages and features provided by one or more embodiments of the invention will become more fully understood from the detailed description given hereinbelow and the appended drawings which are given by way of illustration only, and thus are not intended as a definition of the limits of the present invention.

BRIEF DESCRIPTION OF THE DRAWING

FIG. 1 is a view for describing a configuration of a metal grating for X-ray according to a first embodiment;

FIGS. 2A to 2C are views for describing a cross section of an X-ray absorption portion in a metal grating for X-ray shown in FIG. 1;

FIG. 6 is a view for describing an anodic oxidation method for forming a plurality of holes in a metal substrate;

FIGS. 7A to 7D are views for describing a process for forming a recess, in which part of a partition wall is left in a partition-wall partially leaving/removing step;

FIG. 8 is a view for describing a configuration of a metal grating for X-ray according to a second embodiment;

FIGS. 9A to 9C are views for describing a cross section of an X-ray absorption portion in a metal grating for X-ray shown in FIG. 8;

FIGS. 10A to 10D are views for describing a method for manufacturing the metal grating for X-ray shown in FIG. 8 (No. 1);

FIG. 13 is a perspective view for describing a configuration of a metal grating for X-ray according to a third embodiment;

FIGS. 15A to 15C are views for describing a method for manufacturing the metal grating for X-ray shown in FIG. 13 (No. 1);

DETAILED DESCRIPTION OF EMBODIMENTS

Figure 3C:
FIGS. 3A to 3D are views for describing a method for manufacturing the metal grating for X-ray shown in FIG. 1 (No. 1)

Hereinafter, referring to the drawings, one or a plurality of embodiments of the present invention will be described. However, the scope of the present invention is not limited to the disclosed embodiments. Configurations given the same reference numerals in respective figures show the same configurations, and descriptions thereof are omitted as needed. In the present specification, when a generic term is used, a relevant configuration is denoted by a reference numeral with a suffix omitted, and when an individual configuration is referred to, it is denoted by a reference numeral with a suffix.

The high aspect ratio structure in the present embodiment includes a substrate and a grating formed in the substrate, the grating includes a plurality of projections formed so as to have a spatial period, and each of the plurality of projections includes a plurality of holes extending in a direction crossing a grating surface of the grating. In the present embodiment, as to a partition wall between the holes adjacent to each other in each of the plurality of projections, a thickness thereof is smaller on a bottom side of the holes than that on a grating surface side, and each of a plurality of recesses formed between the plurality of projections includes a porous member, over side wall, including a plurality of holes extending in the direction crossing the grating surface inside the relevant recess and within a predetermined range of the grating surface to a bottom portion of the recess, excluding the bottom portion. As the above-described high aspect ratio structure, for example, a metal grating, a mold for manufacturing an ultrasonic probe, and the like can be cited. Hereinafter, first, as one example of the metal grating, a metal grating for X-ray will be described more specifically, and next, the mold for manufacturing the ultrasonic probe will be described more specifically.

First Embodiment; a Metal Grating for X-Ray as One Example of a High Aspect Ratio Structure, and a Method for Manufacturing the Same FIG. 1 is a perspective view showing a configuration of a metal grating for X-ray according to a first embodiment. FIGS. 2A to 2C are views for describing a cross section of an X-ray absorption portion in the metal grating for X-ray shown in FIG. 1. FIG. 2A schematically shows the cross section of the X-ray absorption portion, FIG. 2B shows an enlarged cross-sectional view of the X-ray absorption portion on the grating surface side (a main surface side), and FIG. 2C shows an enlarged cross-sectional view of the X-ray absorption portion on the bottom side of the holes. In FIG. 1, illustration of a porous member 1121a included in part of an inside of each X-ray transmission portion 112a is omitted.

A metal grating for X-ray 1a shown in FIGS. 1 and 2A to 2C includes a grating region 10a and a frame region 12a provided in a metal substrate 13. The grating region 10a is a region where a grating 11a is formed, and the frame region 12a is provided in a periphery thereof so as to surround this grating region 10a.

If a rectangular coordinate system of DxDyDz is set as shown in FIG. 1, this grating 11a includes a plurality of X-ray absorption portions 111a and a plurality of X-ray transmission portions 112a, the plurality of X-ray absorption portions 111a each having a predetermined thickness (depth) H (a length in a direction Dz perpendicular to a grating surface DxDy (a normal direction of the grating surface DxDy)), and extending linearly in one direction Dx, and the plurality of X-ray transmission portions 112a each having the predetermined thickness H and extending linearly in the one direction Dx. The plurality of X-ray absorption portions 111a and the plurality of X-ray transmission portions 112a are alternately arranged in parallel. Therefore, the plurality of X-ray absorption portions 111a are arranged at predetermined intervals in a direction Dy perpendicular to the one direction Dx. In other words, the respective plurality of X-ray transmission portions 112a are arranged at predetermined intervals in the direction Dy perpendicular to the one direction Dx. This predetermined interval (pitch) P is constant in the present embodiment. That is, the plurality of X-ray absorption portions 111a are arranged at equal intervals P in the direction Dy perpendicular to the one direction Dx. In the present embodiment, the X-ray absorption portions 111a are plate-like or layered along a surface DxDz perpendicular to the surface DxDy, and the plurality of X-ray transmission portions 112a sandwiched between the X-ray absorption portions 111a adjacent to each other are plate-like or layered spaces along the surface DxDz.

In the present embodiment, each of the above-described plurality of X-ray absorption portions 111a includes a plurality of holes PEa extending in the direction crossing the grating surface DxDy of the grating 11a, as shown in FIGS. 2A to 2C. As to a partition wall between the holes PEa adjacent to each other, a thickness thereof becomes smaller on the bottom side of the hole PEa than that on the grating surface DxDy side. In an example shown in FIGS. 2A to 2C, the plurality of holes PEa extend in a direction substantially perpendicular to the grating surface DxDy to be formed inside the X-ray absorption portions 111a, and in the partition wall between the holes PEa adjacent to each other, the thickness thereof gradually becomes smaller from the grating surface DxDy to a bottom portion of the hole PEa along the above-described direction.

In the present embodiment, as shown in FIG. 2A, each of the plurality of X-ray transmission portions 112a includes, over side wall, the porous member 1121a including the plurality of holes PEa extending in the direction crossing the grating surface DxDy inside the transmission portion 112a and within a predetermined range from the grating surface DxDy of the grating 11a to a bottom portion thereof, excluding the bottom portion. Preferably, the predetermined range is a range from the grating surface DxDy to a predetermined first length along the direction. Preferably, the predetermined range is a range from a position at a distance of a predetermined second length from the grating surface DxDy along the direction to a predetermined third length along the direction (the predetermined range is a range located in the middle of a section from the grating surface DxDy to the bottom portion). In order to effectively reduce occurrence of sticking, more preferably, the predetermined range is a range located in a center of the section from the grating surface DxDy to the bottom portion. In order to more effectively reduce the occurrence of the sticking, preferably, in the foregoing high aspect ratio structure, the predetermined range is a range located closer to the grating surface DxDy than the central position in the section from the grating surface DxDy to the bottom portion. While a length of the predetermined range in the direction Dz perpendicular to the grating surface DxDy is set properly in view of prevention of the occurrence of the sticking, it is more preferable that the length is shorter in view of reduction in deterioration of an X-ray transmittance in the X-ray transmission portions 112a. As to the length of the predetermined range in the direction Dz perpendicular to the grating surface DxDy, as one example, if the aspect ratio is 3 or more and 10 or less, it is preferable that the foregoing length is 1% or more and 20% or less of the thickness (the depth) H of the X-ray transmission portions 112a, and if the aspect ratio is 10 or more, it is preferable that the foregoing length is 1% or more and 50% or less of the thickness (depth) H of the X-ray transmission portions 112a. The present embodiment is not limited to this range. In the example shown in FIGS. 2A to 2C, the predetermined range where the porous member 1121a is formed is the range from the position at the distance of the predetermined second length from the grating surface DxDy along the direction Dz perpendicular to the grating surface DxDy to the predetermined third length along the direction Dz (the predetermined range is the range located in the middle of the section from the grating surface DxDy to the bottom portion), more particularly, is the range located closer to the grating surface DxDy than the central position in the section from the grating surface DxDy to the bottom portion, and the plurality of holes PEa formed inside this porous member 1121a extend in the direction substantially perpendicular to the grating surface DxDy. The plurality of holes PEa may extend in the direction substantially perpendicular to the grating surface DxDy while branching, or may extend in the direction substantially perpendicular to the grating surface DxDy without branching.

The plurality of X-ray absorption portions 111a function so as to absorb X-rays, and the plurality of X-ray transmission portions 112a function so as to transmit the X-rays. Therefore, as one aspect, the above-described metal grating for X-ray 1a can be utilized as a normal grating in which the pitch P is sufficiently long to a wavelength of the X-rays to prevent interference fringes from occurring, for example, a 0-th grating in an X-ray Talbot-Lau interferometer. As another aspect, the above-described metal grating for X-ray 1a functions as a diffraction grating by setting the predetermined interval P in accordance with the wavelength of the X-rays, and for example, can be utilized as the first grating and the second grating in an X-ray Talbot interferometer or an X-ray Talbot-Lau interferometer. Each of the X-ray absorption portions 111a has the proper thickness H, for example, so as to be able to sufficiently absorb the X-rays in accordance with a specification. The X-rays generally have high transmissivity, and as a result, a ratio of the thickness H to a width W in each of the X-ray absorption portions 111a (the aspect ratio=thickness/width) is a high aspect ratio of 3 or more. The width W in the X-ray absorption portion 111a is a length in the X-ray absorption portion 111a in the direction (a width direction) Dy perpendicular to the one direction (a longitudinal direction) Dx, and the thickness H is a length of the X-ray absorption portion 111a in the normal direction (a depth direction) Dz of the plane DxDy configured by the one direction Dx and the direction Dy perpendicular to the same.

While in the foregoing, the metal grating for X-ray 1a is an absorption type diffraction grating, the metal grating for X-ray 1a becomes a phase type diffraction grating by configuring the X-ray absorption portion 111a as an X-ray phase portion in which the thickness H is adjusted so as to give predetermined phase change to the X-ray transmission portion 112a.

The above-described metal grating for X-ray 1a is manufactured by a method for manufacturing a high aspect ratio structure including a hole formation step of forming the plurality of holes extending in the direction crossing the main surface in at least the one main surface of the predetermined substrate, a region definition step of periodically defining, in the main surface where the plurality of holes are formed, the plurality of first regions, and the plurality of second regions excluding the plurality of first regions from the main surface, and a partition-wall partially leaving/removing step of immersing the substrate in the etching liquid and thereby removing the partition walls between the plurality of holes formed in the substrate corresponding to the first regions so that part of the partition walls within the predetermined range along the direction, excluding the bottom portions of the plurality of holes are left. Here, in the present embodiment, the hole formation step includes a partition-wall thinning hole formation step of forming the plurality of holes so that the partition wall thickness between the holes adjacent to each other becomes smaller on the bottom side of the holes than that on the main surface side. Each of the recesses is, for example, a slit groove in a one-dimensional grating, a columnar hole (a columnar aperture) in a two-dimensional grating, or the like. Hereinafter, including second to fourth embodiments described later, methods for manufacturing the metal grating for X-ray 1 in which each of the recesses is a slit groove will be described in detail. Even when the recess has another shape such as, for example, a columnar hole shape and the like, the methods are similar.

FIGS. 3A to 3D, 4A to 4D, and 5A to 5D are views for describing a method for manufacturing the metal grating for X-ray in the first embodiment. In FIGS. 3A to 3D, 4A to 4D, and 5A to 5D, FIGS. A and B schematically show each manufacturing step as a pair, and FIG. A are cross-sectional views of FIG. B, while FIG. B are top views. In FIGS. 3A to 3D, 4A to 4D, and 5A to 5D, FIGS. C and D schematically show each manufacturing step as a pair, and FIG. C are cross-sectional views of FIG. D, while FIG. D are top views. FIG. 6 is a view for describing an anodic oxidation method for forming the plurality of holes in the metal substrate. FIGS. 7A to 7D are views for describing a recess formation process in the partition-wall partially leaving/removing step in which the partition wall is partially left. FIG. 7A schematically shows a hole group layer 132 immediately after the wet etching method starts to be carried out, FIG. 7D schematically shows the hole group layer 132 in which part of the partition walls of the plurality of holes PEa are left in first region AR1 by carrying out the wet etching method to form a recess 134 and FIGS. 7B and 7C show the hole group layer 132 in intermediate states between the hole group layer 132 shown in FIG. 7A and the hole group layer 132 shown in FIG. 7D in this order.

Figure 3D:
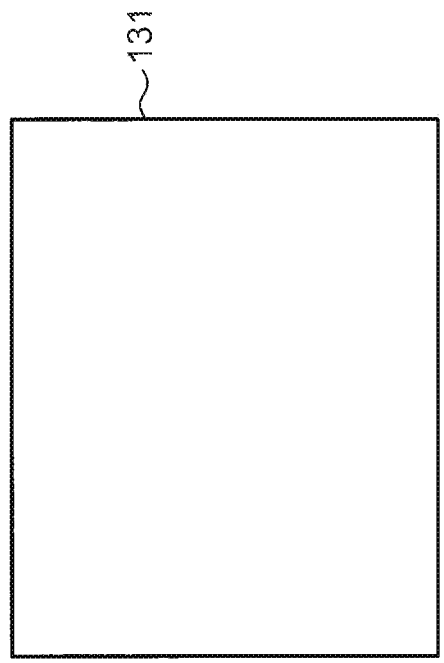
Figure 3A:
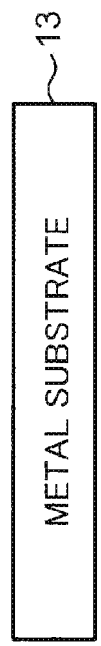
Figure 3B:

In a first method for manufacturing the high aspect ratio structure, in which the metal grating for X-ray 1a is manufactured as one example of the high aspect ratio structure, in order to manufacture this metal grating for X-ray 1a, the plate-like metal substrate 13 is first prepared (FIGS. 3A, 3B).

Next, in at least the one main surface of this metal substrate 13, the plurality of holes PEa extending in the direction crossing the main surface, preferably in the direction substantially perpendicular to the same are formed (the hole formation step). Therefore, the metal substrate 13 is formed of metal (including an alloy) in which the plurality of holes PEa can be formed by an anodic oxidation method or by an anodization method. Here, as one example, a case where the metal substrate 13 is formed of aluminum will be described. In the present embodiment, the hole formation step includes a partition-wall thinning hole formation step of forming the plurality of holes PEa so that the partition wall thickness between the holes PEa adjacent to each other becomes smaller on the bottom side of each of the holes PEa than that on the main surface side. More specifically, in the present embodiment, the hole formation step is configured by the partition-wall thinning hole formation step itself.

More particularly, in the hole formation step configured by the partition-wall thinning hole formation step itself, first, in order to form the plurality of holes in only the one main surface of the metal substrate 13, a protective film 131 is formed on the other main surface (a protective film formation step in the hole formation step, FIGS. 3C, 3D). For example, as the protective film 131, quartz (silicon dioxide, $SiO_2$) film 131 is formed. This quartz film 131 is formed, for example, by various film formation methods such as a chemical vapor deposition (CVD), a sputtering method, and the like, which are publicly known usual practices. For example, in the present embodiment, the quartz film 131 is formed by plasma CVD using tetraethoxysilane. More particularly, first, tetraethoxysilane (TEOS), which is a type of organic silane, is heated, and is bubbled with a carrier gas to thereby generate TEOS gas, and this TEOS gas is mixed with an oxidizing gas such as for example, oxygen, ozone and the like, and a dilution gas such as for example, helium and the like to generate a raw material gas. This raw material gas is introduced into a plasma CVD apparatus, and the quartz film 131 having a predetermined thickness (e.g., 2 μm or the like) is formed on the surface of the metal substrate 13 inside the plasma CVD apparatus.

While in the foregoing, the protective film 131 is the quartz film 131, the present embodiment is not limited thereto. Since the protective film 131 functions as a protective film that protects the metal substrate 13 against a solution used in the anodic oxidation method when the anodic oxidation method is carried out, the protective film 131 only needs to have the above-described function, and it may be formed of a dielectric material such as, for example, silicon nitride (SiN) and the like, a metal film or the like.

Figure 4A:
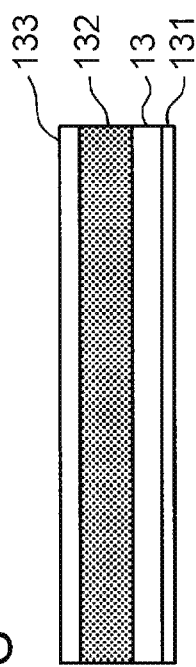
FIGS. 4A to 4D are views for describing the method for manufacturing the metal grating for X-ray shown in FIG. 1 (No. 2)
Figure 4C:
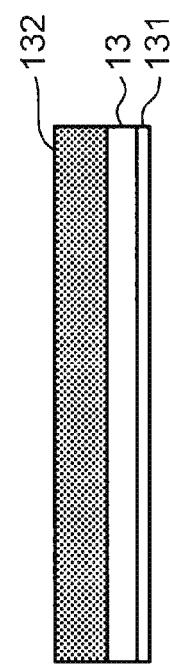
Figure 4B:
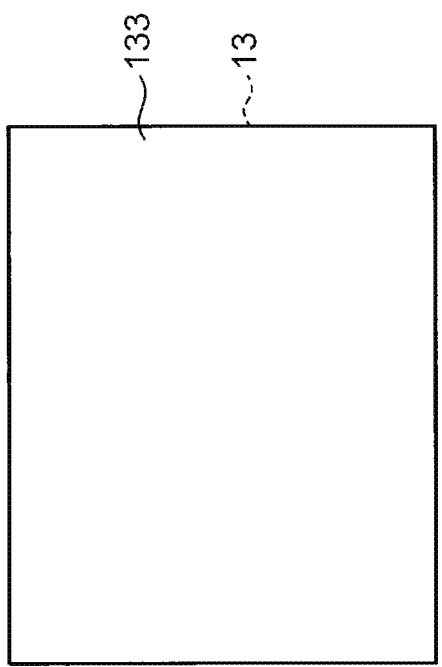
Figure 4D:
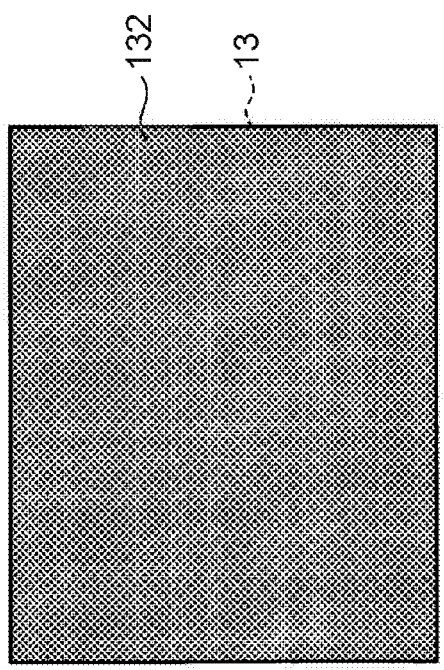

In this hole formation step, next, the hole group layer 132 having the plurality of holes PEa are formed by the anodic oxidation method (or the anodization method) in the one main surface of the metal substrate 13 (an anodic oxidation step (an anodization step) in the hole formation step, FIGS. 4A, 4B). For example, in this anodic oxidation step, as one example, as shown in FIG. 6, an anode of a power supply 21 is conductively connected to the metal substrate 13 with the foregoing protective film 131 formed, a cathode electrode 22 connected to a cathode of the power supply 21, and the metal substrate 13 are immersed in an electrolyte 24 in a tank 23 where the electrolyte 24 is stored. At this time, the cathode electrode 22 and the metal substrate 13 are immersed so that the cathode electrode 22 and the one main surface (the surface not having the protective film 131) of the metal substrate 13 are opposed to each other. It is preferable that the electrolyte 24 is an etching liquid such as an acid solution that has strong oxidizability and dissolves a metal oxide film generated by the anodic oxidation method, for example, phosphoric acid, oxalic acid or the like. It is preferable that the cathode electrode 22 is formed of metal not dissolving in this electrolyte 24, for example, gold (Au), platinum (Pt), carbon (C) or the like. In one example, for the metal substrate 13 formed of aluminum, the electrolyte 24 is oxalic acid of 0.3 M (molarity, mol/l), and the cathode electrode 22 is a titanium plate plated with platinum. When electric conduction is performed, the plurality of holes PEa extending from the main surface to the inside of the metal substrate 13 are formed. In the anodic oxidation method (or the anodization method), the partition wall thickness between the holes PEa adjacent to each other is proportional to a voltage. Therefore, the plurality of holes PEa are formed by the anodic oxidation method (or the anodization method) carried out so that a second applied voltage V2 at the end time is lower than a first applied voltage V1 at the start time (V1>V2). That is, in an electric conduction initial stage, the electric conduction is carried out at a predetermined first voltage value V1, and in an electric conduction end stage, the electric conduction is carried out at a predetermined second voltage value V2 lower than the first voltage value V1 so that the partition wall thickness between the holes PEa adjacent to each other becomes smaller on the bottom side of each of the holes PEa than that on the main surface side. Preferably, this anodic oxidation method (or the anodization method) is carried out at the applied voltage that gradually decreases from the first voltage value V1 to the second voltage value V2 with lapse of time. Preferably, this anodic oxidation method (or the anodization method) is carried out at the applied voltage that decreases at a predetermined ratio from the first voltage value V1 to the second voltage value V2 with lapse of time. Preferably, the predetermined ratio is a predetermined constant value regardless of the lapse of time (the anodic oxidation method (or the anodization method) is carried out at the applied voltage changing and decreasing linearly with a predetermined inclination with the lapse of time. The anodic oxidation method (or the anodization method) is carried out at the applied voltage decreasing at a predetermined constant value per unit time). Preferably, the predetermined ratio is a value changing with the lapse of time (the predetermined inclination is a value changing with the lapse of time. The anodic oxidation method (or the anodization method) in the partition-wall thinning hole formation step is carried out at the applied voltage changing and decreasing nonlinearly with the lapse of time). When the electric conduction is performed in this manner, as shown in FIGS. 2A to 2C, the plurality of holes PEa extending from the main surface of the metal substrate 13 in the thickness direction (the direction Dz, the direction perpendicular to the surface) of the metal substrate 13 are formed at a distance from each other, and the partition wall thickness between the holes PEa adjacent to each other becomes smaller on the bottom side of each of the holes PEa than that on the main surface side. In one example, the electric conduction is carried out with a DC voltage for 20 hours so that the DC voltage is linearly changed from 60 V to 20 V over time (V1=60 V, V2=20 V, −2 V/h). Accordingly, if 10 hours have passed since the electric conduction started, the applied voltage V12 becomes 40 V (V12=40 V). This allows the plurality of holes PEa to be formed, the plurality of holes PEa each having the partition wall thickness between the holes PEa adjacent to each other is about 85 nm on the main surface side, and about 40 nm on the bottom side (a1=about 85 nm (FIG. 2B), a2=about 40 nm (FIG. 2C)). An average distance between centers in the holes PEa adjacent to each other is about 150 nm on the main surface side, and about 50 nm on the bottom side. A thickness of an alumina layer in the bottom portions of the holes PEa is about 20 nm ((a2/2=about 20 nm (FIG. 2C)). A thickness of the hole group layer 132 with the above-described plurality of holes PEa formed is about 110 μm. These holes PEa extend in the direction crossing the main surface while branching by the partition wall thickness changing.

Next, in the main surface where the plurality of holes PEa are formed, the plurality of first regions AR1 and the plurality of second regions AR2 excluding the plurality of the first regions AR1 from the main surface are periodically defined (formed) (the region definition step (a region formation step), FIGS. 4C, 4D, 5A, 5B).

More specifically, in the present embodiment, the region definition step is a resist layer formation step of forming a resist layer 133 on the main surface corresponding to the second regions AR2 of the metal substrate 13. More particularly, first, the resist layer 133 is formed on the main surface of the metal substrate 13, where the plurality of holes PEa are formed (the resist layer formation step, FIGS. 4C, 4D). For example, a dry film resist is pasted onto the main surface of the metal substrate 13 to thereby form the resist layer 133. Next, for example, by using a photolithography technique, the resist layer 133 is patterned, and the resist layer 133 of the patterned portions is removed (a patterning step, FIGS. 5A, 5B). More specifically, a lithography mask not shown is pressed to the resist layer 133, and the resist layer 133 is irradiated with ultraviolet rays through the lithography mask to subject the resist layer 133 to pattern exposure, and be developed. The resist layer 133 of portions not subjected to the pattern exposure (or portions subjected to the pattern exposure) is removed. Thereby, a line and space pattern is formed, in which the resist layer 133 is left in a stripe shape (a striped pattern), for example, with a pitch (a period length) of 5.3 μm and a duty ratio of 50%. This allows the first regions AR1 with the resist layer 133 removed, and the second regions AR2 with the resist layer 133 left (arranged) to be formed in the hole group layer 132 of the metal substrate 13.

The resist layer 133 is neither limited to the dry film resist nor limited to the photoresist, but another resist may be used. This resist layer 133 only needs to function so as to protect the hole group layer 132 of the metal substrate 13 against the etching liquid when the wet etching method in a recess formation step is carried out, so that the resist layer 133 may be formed of an inorganic material or an organic material. For example, after the photoresist is formed on the main surface of the metal substrate 13, where the plurality of holes PEa are formed, and the photoresist is patterned, a metal film (a metal layer) such as, for example, chromium (Cr) film and the like is formed as the resist layer 133. By so-called lift-off (removal of the patterned photoresist), the metal film is patterned. This allows the first regions AR1 with the metal film as the resist layer 133 removed, and the second regions AR2 with the metal film as the resist layer 133 left (arranged) to be formed in the hole group layer 132 of the metal substrate 13.

Figure 5A:
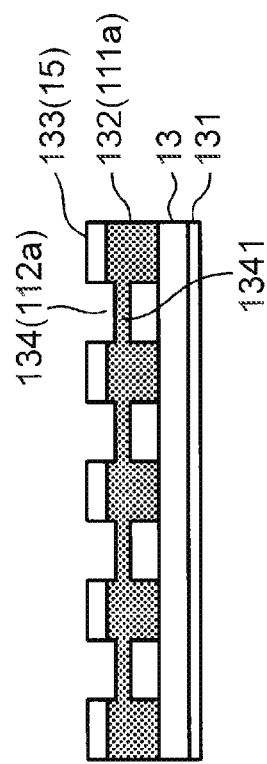
FIGS. 5A to 5D are views for describing the method for manufacturing the metal grating for X-ray shown in FIG. 1 (No. 3)
Figure 5B:
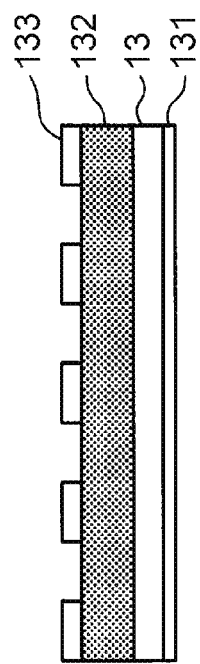
Figure 5C:
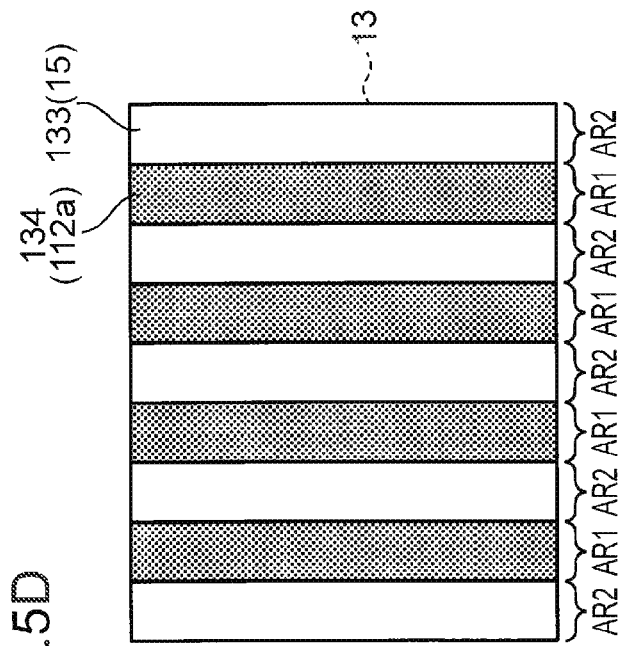
Figure 5D:
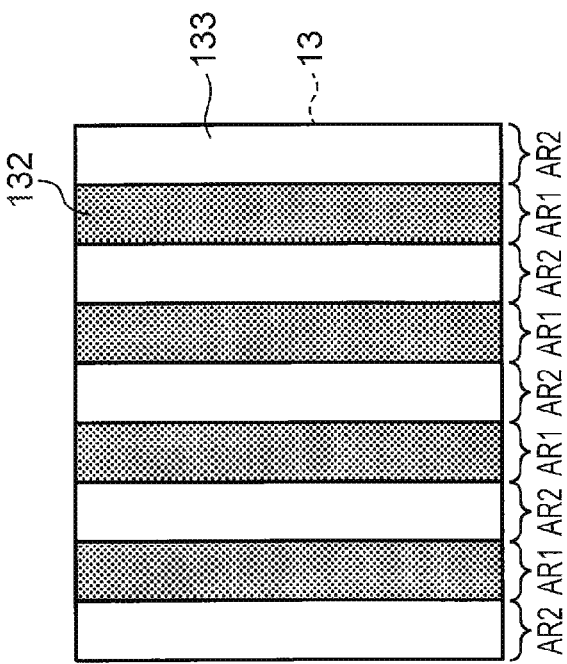

Next, by immersing the metal substrate 13 in the etching liquid, the recesses 134 in which part of the partition walls between the plurality of holes PEa are left are formed in the metal substrate 13 corresponding to the first regions AR1 defined in the region definition step (the partition-wall partially leaving/removing step, FIGS. 5C, 5D). More specifically, the partition-wall partially leaving/removing step is a step of removing the partition walls between the plurality of holes PEa formed in the metal substrate 13 corresponding to the first regions AR1 by immersing the metal substrate 13 in the etching liquid so that part of partition walls 1341 within the predetermined range along the direction crossing the main surface, excluding the bottom portions of the plurality of holes PEa is left. Preferably, the predetermined range is a range from the main surface to the predetermined first length along the direction. Preferably, the predetermined range is a range from the position at the distance of the predetermined second length from the main surface along the direction to the predetermined third length along the direction (the predetermined range is a range located in the middle of the section from the main surface to the bottom portion of each of the plurality of holes PEa). In order to effectively reduce the occurrence of the sticking, more preferably, the predetermined range is a range located in a center of the section from the main surface to the bottom portion of each of the plurality of holes PEa. In order to more effectively reduce the occurrence of the sticking, preferably, the predetermined range is a range located closer to the main surface than the central position in the section from the main surface to the bottom portion of each of the plurality of holes PEa. While a length of the predetermined range in the direction perpendicular to the main surface is set properly in view of prevention of the occurrence of the sticking, as described later, it is more preferable that the length is shorter in view of reduction in deterioration of an X-ray transmittance because the recesses 134 formed in this partition-wall partially leaving/removing step become the X-ray transmission portions 112a. As to the length of the predetermined range in the direction Dz perpendicular to the main surface (i.e., the grating surface DxDy), as one example, if the aspect ratio is 3 or more and 10 or less, it is preferable that the length is 1% or more and 20% or less of the thickness (the depth) H of each of the recesses 134 (the X-ray transmission portion 112a), and if the aspect ratio is 10 or more, it is preferable that the length is 1% or more and 50% or less of the thickness (the depth) H of the relevant recess 134 (the X-ray transmission portion 112a).

In one example, the metal substrate 13 after the region definition step is immersed in phosphoric acid liquid (the etching liquid) of 8 vol %, and is left for 150 minutes. At this time, as shown in FIG. 7A, several seconds to several minutes after the immersion of the metal substrate 13, the phosphoric acid liquid permeates the holes PEa of the hole group layer 132 exposed by the patterning step of the region definition step. Thereafter, as shown in FIGS. 7B and 7C, inside each of the holes PEa, the phosphoric acid liquid etches each of the partition walls between the holes PEa adjacent to each other isotropically to dissolve the partition wall with the partition wall 1341 in the predetermined range left, using all the remaining time (≈150 minutes). This allows the slit groove-like recess 134 to be formed in the first region AR1 in the metal substrate 13, in which recess 134 the part of the partition wall 1341 between the plurality of holes PEa is left in the predetermined range, as shown in FIG. 7D (FIGS. 5C and 5D). In this example, the predetermined range is a range from the position at the distance of the predetermined second length from the main surface along the direction Dz perpendicular to the main surface to the predetermined third length along the direction Dz (the range located in the middle of the section from the main surface to the bottom portion of each of the plurality of holes PEa), and more particularly, the range located closer to the main surface than the central position in the section from the main surface to the bottom portion of each of the plurality of holes PEa. Since the partition-wall partially leaving/removing step is carried out by the etching as described above, the length in the direction Dz in the predetermined range is not necessarily constant over the direction Dx, and is not necessarily constant in the direction Dy (that is, both end surfaces of the part of the partition wall 1341 left in this partition-wall partially leaving/removing step are not planes). However, in one example, the predetermined range is within a range of about 5 μm to about 40 μm from the main surface in the direction Dz.

The resist layer 133 left in each of the second regions AR2 is then removed (a resist layer removal step).

Through the above-described manufacturing steps, the hole group layer 132 of the second regions AR protected and left by the resist layer 133 in the partition-wall partially leaving/removing step becomes the X-ray absorption portions 111a (or the X-ray phase portions) of the grating 11a, the recesses 134 in the first regions AR, where the part of the partition walls 1341 are left, become the X-ray transmission portions 112a of the grating 11a, and the left part of the partition walls 1341 become the porous members 1121a, so that the metal grating for X-ray 1a having the configuration shown in FIG. 1 is manufactured. The metal grating for X-ray 1a may be configured such that the resist layer 133 is not removed (the resist layer removal step is omitted) to serve as a protective layer 15 that protects top portions of the X-ray absorption portions 111a, as indicated by broken line in FIG. 1.

Figure 31:
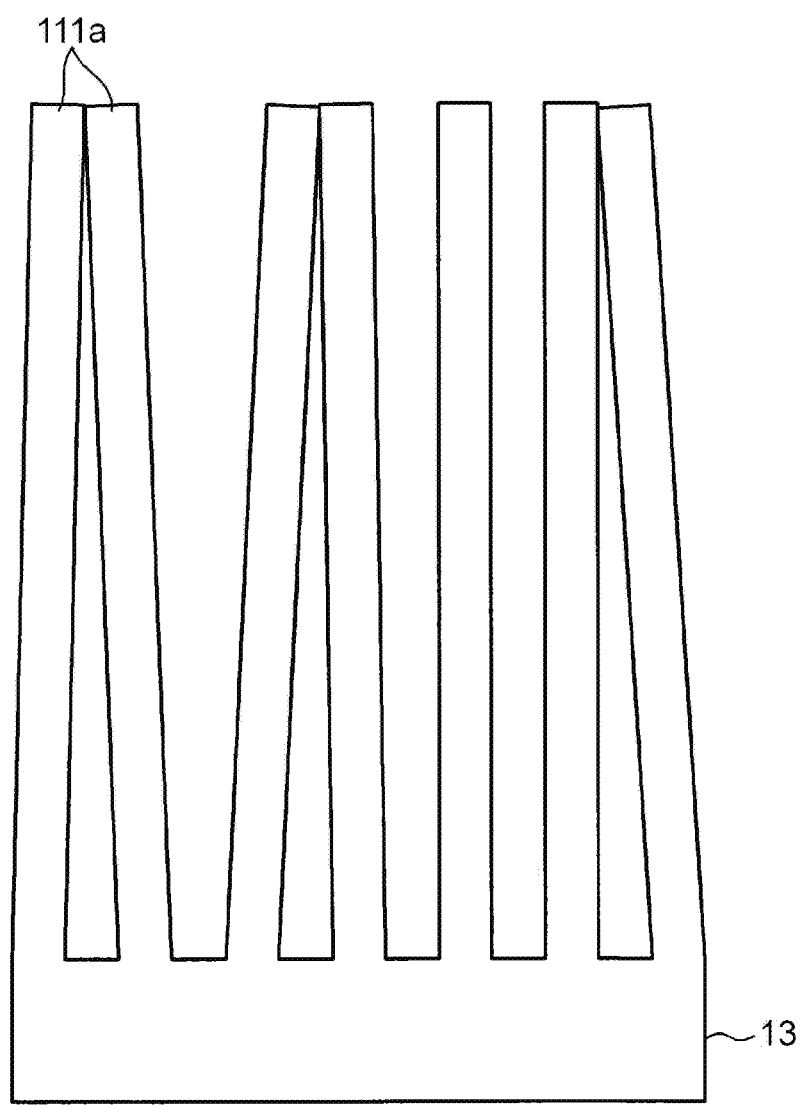
FIG. 31 is a view for describing projections where sticking occurs.

In conventional normal wet etching, for example, as shown in FIG. 31, the sticking occurs during drying of the etching liquid. However, since the first method for manufacturing the high aspect ratio structure in the present embodiment includes the partition-wall partially leaving/removing step, in which by immersing the metal substrate 13 in the etching liquid, the partition walls between the plurality of holes PEa formed in the metal substrate 13 corresponding to the first regions AR1 are removed so as to leave the part of the partition walls 1341 within the predetermined range along the direction crossing the main surface excluding the bottom portions of the plurality of holes PEa, the first regions AR1 are supported by the porous members 1121a (1341) each including the plurality of holes PEa and left within the predetermined range, so that even if the metal substrate 13 corresponding to the first regions AR1 are subjected to the etching, the occurrence of the sticking can be reduced more. In addition, since the first method for manufacturing the high aspect ratio structure includes the partition-wall thinning hole formation step of forming the plurality holes PEa so that the partition wall thickness between the holes PEa adjacent to each other becomes smaller on the bottom side of each of the holes PEa than that on the main surface side, the partition walls on the bottom surface side having the relatively smaller partition wall thickness can be removed dominantly with the lapse of etching time when the wet etching method is carried out, and when the partition walls on the bottom surface side are dissolved and removed, the partition walls on the surface side having the relatively larger partition wall thickness can be left, so that in the partition-wall partially leaving/removing step, the part of the partition walls 1341 can be easily left within the predetermined range along the direction crossing the main surface, excluding the bottom portions of the plurality of holes PEa.

In the first method for manufacturing the high aspect ratio structure, by forming the resist layer 133 on the main surface corresponding to the second regions AR2, the second regions AR2, where the partition walls are not removed in the partition-wall partially leaving/removing step, can be defined (formed), and the region definition step can be easily implemented in the resist layer formation step.

In the anodic oxidation method or the anodization method, the partition wall thickness between the holes PEa adjacent to each other is proportional to the voltage. In order to use this characteristic of the anodic oxidation method or the anodization method, the first method for manufacturing the high aspect ratio structure uses the anodic oxidation method or the anodization method in the partition-wall thinning hole formation step of the hole formation step, and the applied voltage in the anodic oxidation method or the anodization method is adjusted so that the second applied voltage V2 at the end time is lower than the first applied voltage V1 at the start time. Accordingly, because of the characteristic of the anodic oxidation method or the anodization method, in the first method for manufacturing the high aspect ratio structure, the plurality of holes can be easily formed in the main surface of the substrate 13, the plurality of holes having the partition wall thickness between the holes PEa adjacent to each other smaller on the bottom side of the holes PEa than that on the main surface side.

Next, another embodiment will be described.

Second Embodiment; a Metal Grating for X-Ray as One Example of a High Aspect Ratio Structure, and a Method for Manufacturing the Same While in the first embodiment, the second and first regions AR2, AR1 are defined by presence or absence of the resist layer 133 (15), in second embodiment, they may be defined by presence or absence of closing of the plurality of holes in place of the resist layer 133 (15).

FIG. 8 is a perspective view showing a configuration of a metal grating for X-ray according to a second embodiment. FIGS. 9A to 9C are views for describing a cross section of an X-ray absorption portion in the metal grating for X-ray shown in FIG. 8. FIG. 9A schematically shows the cross section of the X-ray absorption portion, FIG. 9B shows an enlarged cross-sectional view of the X-ray absorption portion on a grating surface side (a main surface side), and FIG. 9C shows an enlarged cross-sectional view of the X-ray absorption portion on a bottom side of the holes. In FIG. 8, illustration of a porous member 1121*b* included in a part of an inside of each X-ray transmission portion 112*b* is omitted.

A metal grating for X-ray 1*b* shown in FIGS. 8 and 9A to 9C includes a grating region 10*b* and a frame region 12*b* provided in the metal substrate 13. The grating region 10*b* is a region where the grating 11*b* is formed, and the grating 11*b* includes a plurality of X-ray absorption portions 111*b* and the plurality of X-ray transmission portions 112*b*. Each of the plurality of X-ray transmission portions 112*b* includes the porous member 1121*b* in a predetermined range thereinside. The grating region 10*b*, the frame region 12*b*, the grating 11*b*, the plurality of X-ray absorption portions 111*b*, the plurality of X-ray transmission portions 112*b*, and the porous members 1121*b* in the metal grating for X-ray 1*b* of the second embodiment are similar to the grating region 10*a*, the frame region 12*a*, the grating 11*a*, the plurality of X-ray absorption portions 111*a*, the plurality of X-ray transmission portions 112*a*, and the porous members 1121*a* in the metal grating for X-ray 1*a* of the first embodiment, except that a closing member (refer to FIGS. 12B to 12E) used in place of the resist layer 133 of the first embodiment is provided in each of the plurality of X-ray absorption portions 111*b*, and thus, descriptions thereof are omitted.

The closing members are members closing the plurality of holes PEa formed so as to extend in the direction crossing a grating surface of the grating 11*b* (the main surface of the metal substrate 13), as indicated by oblique lines in FIGS. 9A and 9B.

The above-described metal grating for X-ray 1*b* is manufactured by a method for manufacturing a high aspect ratio structure, including the hole formation step configured by the partition-wall thinning hole formation step itself, the region definition step (the region formation step), and the partition-wall partially leaving/removing step. Here, in the present embodiment, the region definition step includes a closing step of closing one or the plurality of holes formed in a portion corresponding to each of the second regions of the plurality of holes.

FIGS. 10A to 10D, and 11A to 11D are views for describing a method for manufacturing the metal grating for X-ray in the second embodiment. In FIGS. 10A to 10D, and 11A to 11D, FIGS. A and B schematically show each manufacturing step as a pair, and FIG. A are cross-sectional views of FIG. B, while FIG. B are top views. In FIGS. 10A to 10D, and 11A to 11D, FIGS. C and D schematically show each manufacturing step as a pair, and FIG. C are cross-sectional views of FIG. D, while FIG. D are top views. FIGS. 12A to 12E are views for describing sealing treatment in the closing step.

In a second method for manufacturing a high aspect ratio structure, in which the metal grating for X-ray 1*b* is manufactured as one example of the high aspect ratio structure, in order to manufacture this metal grating for X-ray 1*b*, first, the metal substrate 13 is prepared similar to the above-described first method for manufacturing the metal grating for X-ray 1*a*, and next, the hole formation step is carried out, the hole formation step including the protective film formation step and the anodic oxidation step (or the anodization step), and configured by the partition-wall thinning hole formation step itself. This anodic oxidation step (or the anodization step) is carried out in the same conditions as those of the first embodiment, which allows the hole group layer 132 similar to that of the first embodiment to be formed.

Next, in the main surface where the plurality of holes PEa are formed, the plurality of first regions AR1 and the plurality of second regions AR2 excluding the plurality of the first regions AR1 from the main surface are periodically defined (formed) (the region definition step (a region formation step), FIGS. 10A to 10D).

More specifically, in the present embodiment, the region definition step is the closing step of closing one or the plurality of holes formed in a portion corresponding to each of the second regions AR2 of the plurality of holes PEa in the hole group layer 132. The closing step, more specifically, includes a first step of forming a second resist layer 135 on the main surface, a second step of patterning the second resist layer 135 to remove the second resist layer 135 corresponding to the second regions AR2, a third step of closing the one or the plurality of holes PEa, of the plurality of holes PEa in the hole group layer 132, in each of the second regions AR2 with the second resist layer 135 removed in the second step, and a fourth step of removing the second resist layer 135 left after the second step. This second resist layer 135 only needs to function so as to protect the one or the plurality of holes PEa formed in each of the first regions AR1 when the one or the plurality of holes PEa formed in each of the second regions AR2 are closed, and may be formed of an inorganic material or an organic material.

More specifically, first, a dry film resist made of, for example, an organic material is pasted onto the main surface of the metal substrate 13 with the hole group layer 132 formed to thereby form the second resist layer 135 (the first step).

Next, for example, by using a photolithography technique, the second resist layer 135 is patterned, and the second resist layer 135 corresponding to the second regions AR2 is removed (the second step, FIGS. 10A, 10B). More specifically, a lithography mask not shown is pressed to the second resist layer 135, and the second resist layer 135 is irradiated with ultraviolet rays through the lithography mask to subject the second resist layer 135 to pattern exposure, and be developed. The second resist layer 135 of portions not subjected to the exposure (or portions subjected to the exposure) is removed. Thereby, a line and space pattern is formed, in which the second resist layer 135 is left in a stripe shape, for example, with a pitch (a period length) of 5.3 μm and a duty ratio of 50%.

Figure 12A:
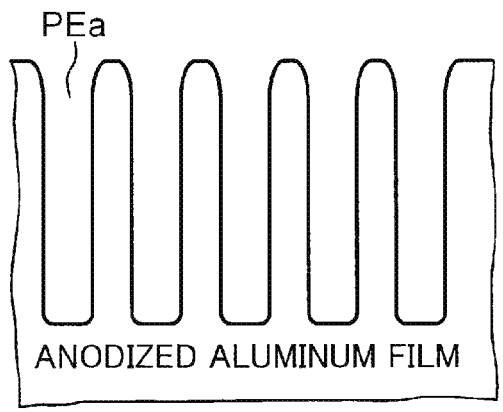
FIGS. 12A to 12E are views for describing sealing treatment in a closing step.
Figure 12B:
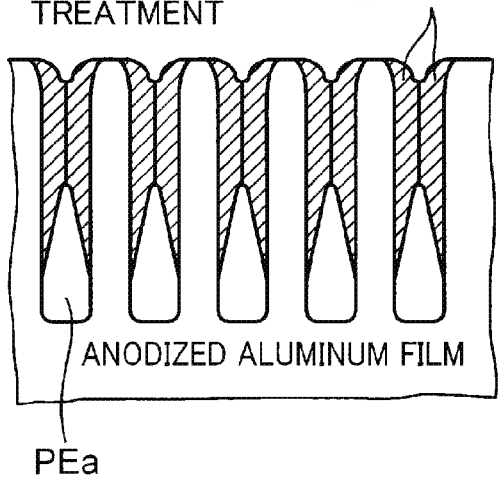
Figure 12C:
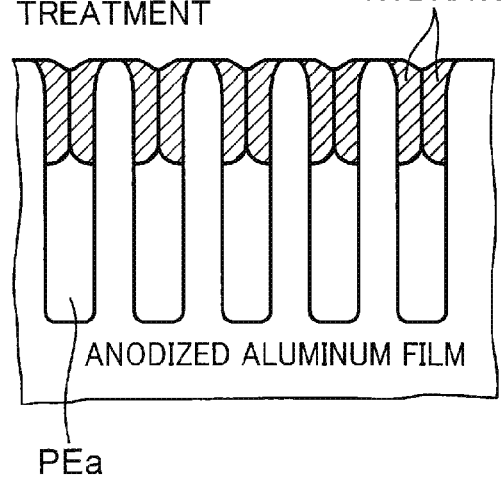
Figure 12D:
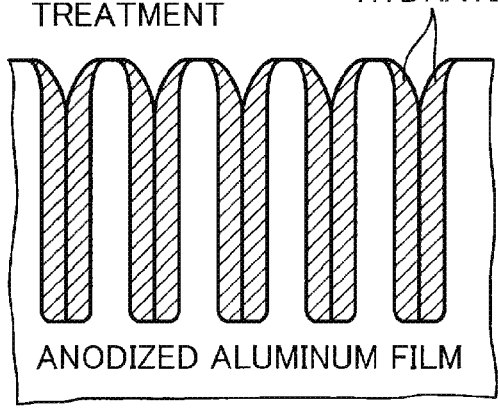
Figure 12E:
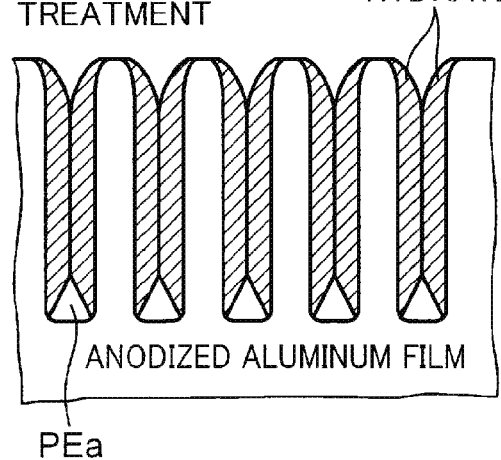

Next, of the plurality of holes PEa in the hole group layer 132, opening(s) in the one or the plurality of holes PEa formed in the region (each of the second regions AR2) with the second resist layer 135 removed in the second step is (are) closed, so that a closed hole group layer 136 is formed (the third step, FIGS. 10C, 10D). For example, the holes PEa are closed by hole-sealing treatment using a hole-sealing material. More specifically, the metal substrate 13 after the second step is immersed in pure water (boiling water) at 98° C. for one hour. Thereby, in the plurality of holes PEa in the relevant second region AR2 with the second resist layer 135 removed as shown in FIG. 12A, as shown in FIGS. 12B to 12E, in respective aspects of the figures, a volume of alumina is expanded by a hydrate of alumina generated with the boiling water, so that at least the openings of the holes PEa are closed. More preferably, the whole insides of the holes PEa are filled with the hydrate of alumina (charged), as shown in FIG. 12D. On the other hand, in the plurality of holes PEa formed in the regions (the first regions AR1) with the second resist layer 135 left (arranged), the second resist layer 135 prevents the boiling water from entering the holes PEa, so that the relevant plurality of holes PEa are not closed.

The hole-sealing treatment is not limited to the above-described boiling pure water method using the boiling water, but as shown in table 1, the method may be another method such as a nickel acetate method using a hole-sealing material such as, for example, a top seal H298 made by OKUNO CHEMICAL INDUSTRIES CO., LTD, and the like.

Figure 11A:
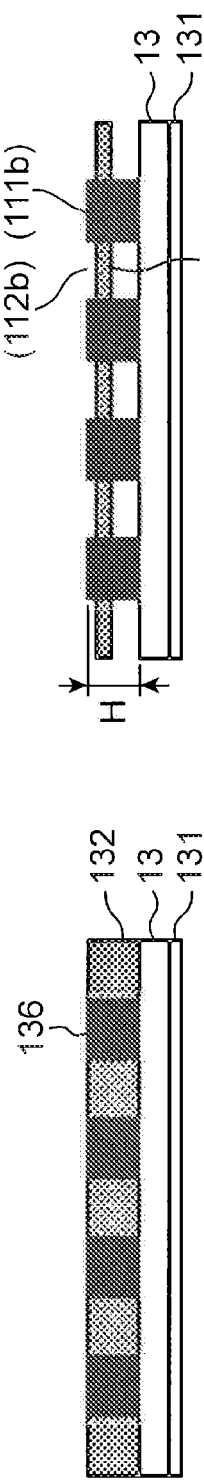
FIGS. 11A to 11D are views for describing the method for manufacturing the metal grating for X-ray shown in FIG. 8 (No. 2)
Figure 11B:
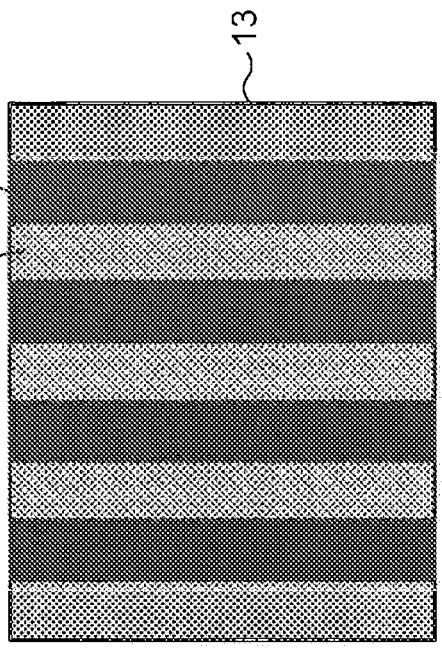

In this manner, the region definition step including the closing step is carried out, and in the main surface of the metal substrate 13, the first regions AR1 and the second regions AR2 are defined (formed), the first regions AR1 including the hole group layer 132 made of the holes PEa whose openings are not closed (in the present embodiment, the holes are not sealed) to become each a region where a recess 137 will be formed in the partition-wall partially leaving/removing step, and the second regions AR2 including the closed hole group layer 136 made of the holes PEa whose openings are closed (in the present embodiment, the holes are sealed) to become each a region where a recess 137 will not be formed in the partition-wall partially leaving/removing step (FIGS. 11A, 11B). The first regions AR1 of the hole group layer 132 and the second regions AR2 of the closed hole group layer 136 are arranged alternately side by side at a pitch having a period 5.3 μm in this example.

Figure 11C:
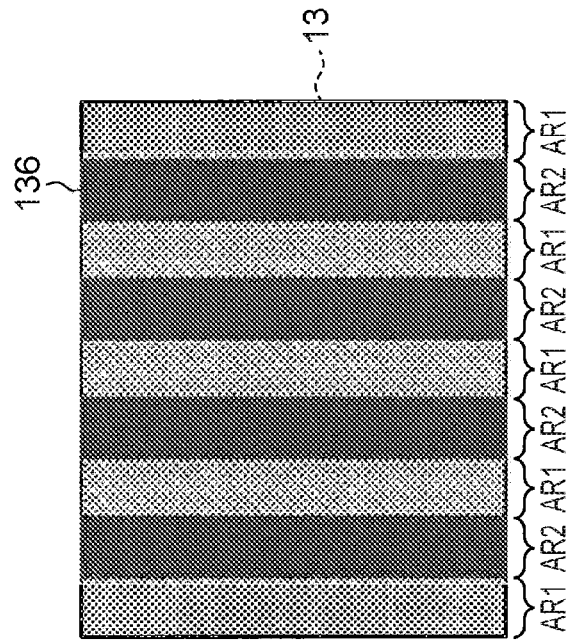
Figure 11D:
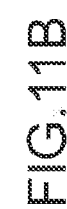

Next, by the wet etching method in which the metal substrate 13 is immersed in the etching liquid, the recesses in which part of the partition walls between the plurality of holes PEa are left are formed in the metal substrate 13 corresponding to the first regions AR1 (the partition-wall partially leaving/removing step, FIGS. 11C, 11D). In one example, the metal substrate 13 is immersed in phosphoric acid liquid (the etching liquid) of 8 vol %, and is left for 150 minutes similar to the first embodiment. Similar to the first embodiment, this allows the partition walls between the holes PEa adjacent to each other to be etched, and the partition walls to be dissolved with the partition walls 1371 in the predetermined range left. Thereby, in the first regions AR1 in the metal substrate 13 are formed the plurality of slit groove-like recesses 137 in which the part of the partition walls 1371 between the plurality of holes PEa are left in the predetermined range.

Through the above-described manufacturing steps, the plurality of recesses 137 with the part of the partition walls 1371 left are formed, by which the plurality of plate-like, closed hole group layers 136 left in the second regions AR2 become the X-ray absorption portions 111b (or the X-ray phase portions) of the grating 11b, the plurality of recesses 137 with the part of the partition walls 1371 left in the first

TABLE 1

| CONDITION | STEAM METHOD | PURE BOILING WATER METHOD | NICKEL ACETATE METHOD | BICHROMIC ACID METHOD | SODIUM SILICATE METHOD |
|---|---|---|---|---|---|
| TREATMENT BATH | PRESSURIZED STEAM | PURE WATER | NICKEL ACETATE 5~5.8 g/l COBALT ACETATE 1 g/l BORIC ACID 8~84 g/l | POTASSIUM DICHROMATE 15 g/l SODIUM CARBONATE 4 g/l | SODIUM SILICATE METHOD |
| pH | — | 6~9 | 5~6 | 6.5~7.5 | — |
| TEMPERATURE (° C.) | (2~5 kg cm²) | 90~100 | 70~90 | 90~95 | 90~100 |
| TIME (min) | 15~30 | 15~30 | 15~20 | 2~10 | 20~30 |

Next, the second resist layer 135 of the first regions AR1 left after the second step is removed (the fourth step, FIGS. 11A, 11B). For example, the second resist layer 136 left after the second step is removed with a remover liquid dedicated to a dry film.

regions AR1 left become the X-ray transmission portions 112b of the grating 11b, and the left part of the partition walls 1371 become the porous members 1121b, so that the metal grating for X-ray 1b having the configuration shown in FIGS. 8 and 9A to 9C is manufactured.

As described above, the second method for manufacturing the high aspect ratio structure, in which as one example, the metal grating for X-ray 1b is manufactured exerts actions and effects similar to those of the first method for manufacturing the high aspect ratio structure, in which the metal grating for X-ray 1a in the first embodiment is manufactured, except for effects in the foregoing resist formation step.

In the second method for manufacturing the high aspect ratio structure, by closing the one or more the plurality of holes PEa formed in the portion corresponding to each of the second regions AR2 of the plurality of holes PEa, the second regions AR2 where the recesses are not formed in the partition-wall partially leaving/removing step can be defined (formed), and the region definition step can be easily implemented in the closing step. In the second method for manufacturing the high aspect ratio structure, since the closing step prevents the etching liquid from entering the holes PEa when the wet etching method is carried out, the resist layer against the etching liquid, which is normally required when the wet etching method is carried out, becomes unnecessary. Therefore, in the second method for manufacturing the high aspect ratio structure, so-called undercut by the resist layer, which normally occurs when the wet etching method is carried out, does not occur, and the etching liquid permeates to the bottom portions of the holes PE to dissolve the partition walls formed between the holes PEa adjacent to each other. Accordingly, in the second method for manufacturing the high aspect ratio structure, the high aspect ratio structure having the recesses 137 each having side surfaces substantially perpendicular to the main surface of the metal substrate 13 can be manufactured by the wet etching method.

Next, another embodiment will be described.

Third Embodiment; a Metal Grating for X-Ray as One Example of a High Aspect Ratio Structure, and a Method for Manufacturing the Same While in the foregoing metal grating for X-rays 1a, 1b in the first and second embodiments, a position of the bottoms in the plurality of recesses 134, 137, which are slit groove-like spaces (a recess bottom position) is substantially the same as a position of the bottoms in the plurality of holes PEa formed in the plurality of plate-like (layered) hole group layers 132, 136 left by the formation of the plurality of recesses 134, 137 (a hole bottom position), in a metal grating for X-ray 1c in a third embodiment, in the direction Dz, a recess bottom position in a plurality of recesses 140, which are slit groove-like spaces, is lower than a hole bottom position in a plurality of holes PEb formed in a plurality of plate-like (layered) hole group layers 138 left by the formation of the plurality of recesses 140. That is, the depth H of the recesses 140 is larger than the depth of the holes PEb.

Figure 14:
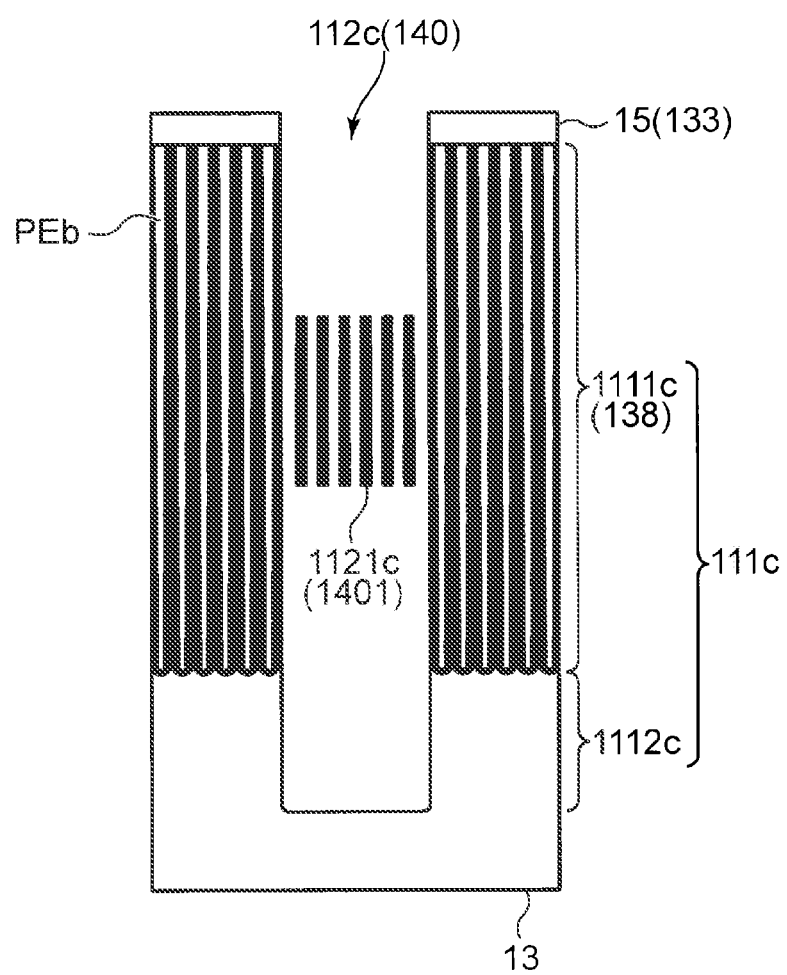
FIG. 14 is a view for describing a cross section of an X-ray absorption portion in a metal grating for X-ray shown in FIG. 13.

FIG. 13 is a view for describing a configuration of a metal grating for X-ray according to a third embodiment. FIG. 14 is a view for describing a cross section of an X-ray absorption portion in the metal grating for X-ray shown in FIG. 13. In FIG. 13, illustration of a porous member 1121c included in part of an inside of each X-ray transmission portion 112c is omitted.

The metal grating for X-ray 1c shown in FIGS. 13 and 14 includes a grating region 10c and a frame region 12c provided in the metal substrate 13. The grating region 10c is a region where the grating 11c is formed, and the grating 11c includes a plurality of X-ray absorption portions 111c and the plurality of X-ray transmission portions 112c. Each of the plurality of X-ray transmission portions 112c includes a porous member 1121c in a predetermined range thereinside. The grating region 10c, the frame region 12c, the grating 11c, the plurality of X-ray absorption portions 111c, the plurality of X-ray transmission portions 112c, and the porous members 1121c in the metal grating for X-ray 1c of the third embodiment are similar to the grating region 10a, the frame region 12a, the grating 11a, the plurality of X-ray absorption portions 111a, the plurality of X-ray transmission portions 112a, and the porous members 1121a in the metal grating for X-ray 1a of the first embodiment, except that the partition wall thickness in the plurality of holes PEb formed in the plurality of X-ray absorption portions 111c and the hole bottom position in the plurality of holes PEb are different from those in the first embodiment, and thus, descriptions thereof are omitted.

In the present embodiment, as shown in FIG. 14, each of the plurality of X-ray absorption portions 111c includes the plurality of holes PEb extending to the middle of the relevant X-ray absorption portion 111c in the direction crossing the grating surface DxDy of the grating 11c, and the partition walls between the holes PEb adjacent to each other are substantially equal in the direction Dz in an ideal case, or a thickness thereof becomes larger on the bottom side of the holes PEb than that on the grating surface DxDy. In this manner, since the plurality of holes PEb extend to the middle of the X-ray absorption portions 111c in the direction crossing the grating surface DxDy of the grating 11c, each of the plurality of X-ray absorption portions 111c includes a first portion 1111c where the plurality of holes PEb are formed thereinside in the direction Dz, and a second portion 1112c where the plurality of holes PEb are not formed inside continuous to the first portion 1111c, that is, which is formed of only the metal substrate 13. In the example shown in FIG. 14, the plurality of holes PEb extend in the direction Dz substantially perpendicular to the grating surface DxDy to the middle of the X-ray absorption portions 111c to be formed inside each of the X-ray absorption portions 111c, and as to the partition walls between the holes PEb adjacent to each other, the thickness thereof gradually becomes larger from the grating surface DxDy to bottom portions of the holes PEb along the above-described direction.

The above-described metal grating for X-ray 1c is manufactured by a method for manufacturing a high aspect ratio structure including the hole formation step, the region definition step (the region formation step), and the partition-wall partially leaving/removing step. Here, in the present embodiment, the hole formation step includes a first hole formation step carried out before the region definition step is carried out, and a second hole formation step carried out after the region definition step is carried out, and the second hole formation step is the partition-wall thinning hole formation step of further forming a plurality of holes PEc so as to further extend in the direction continuously to the respective plurality of holes PEb formed in the first hole formation step.

FIGS. 15A to 15C and 16A to 16C are views for describing a method for manufacturing the metal grating for X-ray in the third embodiment. In FIGS. 15A to 15C and 16A to 16C, FIG. A are cross-sectional views of FIG. B, and FIG. B are top views, and FIG. C are enlarged cross-sectional views in each of which a part of FIG. B is enlarged.

In a third method for manufacturing a high aspect ratio structure, in which the metal grating for X-ray 1c is manufactured as one example of the high aspect ratio structure, in order to manufacture this metal grating for X-ray 1c, the metal substrate 13 is prepared similar to the foregoing first method for manufacturing the metal grating for X-ray 1*a*, and next, the first hole formation step is carried out.

In this first hole formation step, in at least the one main surface of this metal substrate 13, the plurality of holes PEb extending in the direction crossing the main surface, preferably in the direction substantially perpendicular to the same are formed. In the present embodiment, in the first hole formation step, the plurality of holes PEb are formed so that the partition wall thickness between the holes PEb adjacent to each other is substantially equal in the direction Dz in an ideal case, or the thickness thereof becomes larger on the bottom side of the holes PEb than that on the main surface side.

More particularly, in the first hole formation step, first, in order to form the plurality of holes in only the one main surface of the metal substrate 13, a protective film 131 is formed on the other main surface similar to the first embodiment (a protective film formation step in the first hole formation step). For example, as the protective film 131, quartz (silicon dioxide, $SiO_2$) film 131 is formed by a publicly-known film formation method.

In this first hole formation step, next, the hole group layer 138 having the plurality of holes PEb is formed by the anodic oxidation method (or the anodization method) in the one main surface of the metal substrate 13 (the anodic oxidation step (or the anodization step) in the first hole formation step). This anodic oxidation step (or the anodization step) is carried out in different conditions from those in the first embodiment. In one example, as shown in FIG. 6, the anode of the power supply 21 is conductively connected to the metal substrate 13 having the protective film 131, the cathode electrode 22 connected to the cathode of the power supply 21, and the metal substrate 13 are immersed in the electrolyte 24 in the tank 23 where the electrolyte 24 is stored so that the cathode electrode 22 and the one main surface (the surface not having the protective film 131) of the metal substrate 13 are opposed. In the present embodiment, electric conduction is carried out at a constant voltage value V3 from the start time to the end time. Thereby, the plurality of holes PEb extending from the main surface to the inside of the metal substrate 13 are formed, and the plurality of holes PEb are formed so that the partition wall thickness between the holes PEb adjacent to each other is substantially equal in the direction Dz in an ideal case, or the thickness thereof becomes larger on the bottom side of the holes PEb than that on the main surface side. In one example, for the metal substrate 13 formed of aluminum, the electrolyte 24 is oxalic acid of 0.3 M (molarity, mol/l), and the cathode electrode 22 is a titanium plate plated with platinum. Electric conduction is carried out at a constant voltage value 60 V for 9 hours from the start time to the end time. When the above-described electric conduction is performed in this manner, as shown in FIG. 14, the plurality of holes PEb extending from the main surface of the metal substrate 13 in the thickness direction (the direction Dz, the direction perpendicular to the surface) of the metal substrate 13 are formed at a distance from each other, and the partition wall thickness between the holes PEb adjacent to each other becomes larger on the bottom side of the holes PEb than that on the main surface side. This allows the plurality of holes PEb to be formed, the plurality of holes PEb each having the partition wall thickness between the holes PEb adjacent to each other is about 85 nm on the main surface side, and about 120 nm on the bottom side. An average distance between centers in the holes PEb adjacent to each other is about 150 nm regardless of the thickness in the thickness direction (the direction Dz) of the metal substrate 13. A thickness of the hole group layer 138 with the above-described plurality of holes PEb formed is about 110 μm.

Next, in the main surface where the plurality of holes PEb are formed, the plurality of first regions AR1 and the plurality of second regions AR2 excluding the plurality of the first regions AR1 from the main surface are periodically defined (formed) (the region definition step (the region formation step), FIGS. 15A to 15C). More specifically, similar to the region definition step in the first embodiment, the resist layer formation step using the dry film resist is carried out, and the patterning step of patterning the foregoing resultant is carried out. As shown in FIGS. 15A to 15C, a line and space pattern is formed, in which the resist layer 133 is left in a stripe shape, for example, with a pitch (a period length) of 5.3 μm and a duty ratio of 50%. This allows the first regions AR1 with the resist layer 133 removed, and the second regions AR2 with the resist layer 133 left (arranged) to be formed in the hole group layer 138 of the metal substrate 13.

Figure 16A:
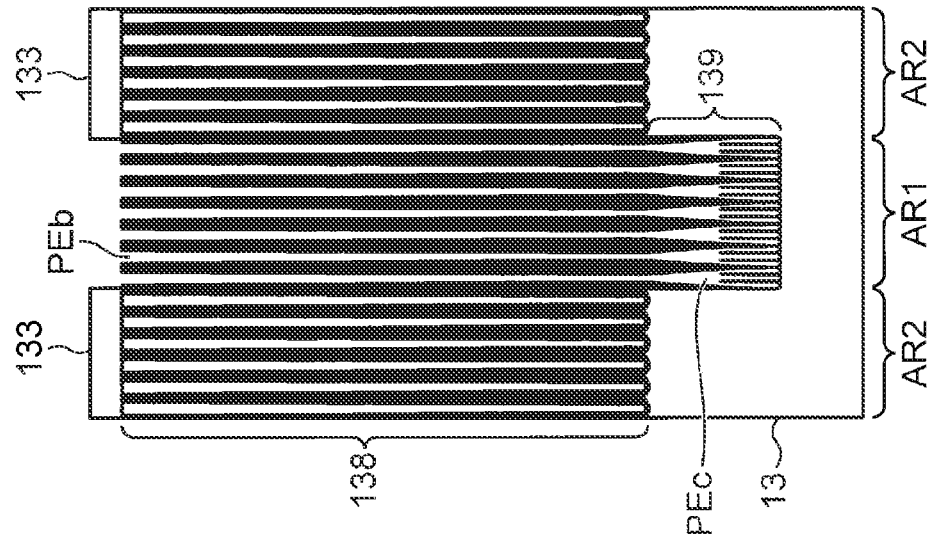
FIGS. 16A to 16C are views for describing the method for manufacturing the metal grating for X-ray shown in FIG. 13 (No. 2)
Figure 16B:
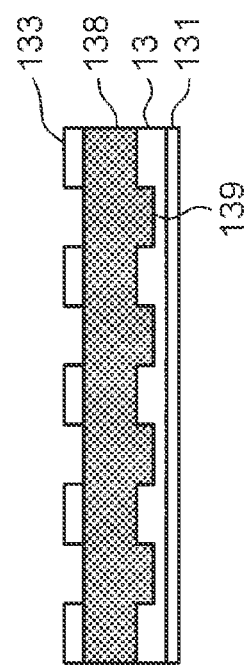
Figure 16C:
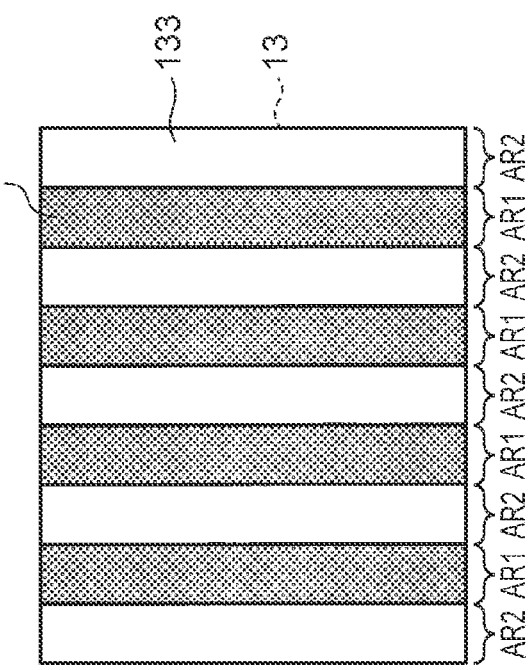

Next, the second hole formation step is carried out. This second hole formation step is the partition-wall thinning hole formation step of further forming the plurality of holes PEc so as to further extend in the direction continuously to the respective holes PEb formed in the first hole formation step (FIGS. 16A to 16C). That is, in this second hole formation step configured by the partition-wall thinning hole formation step itself, similar to the first embodiment, the plurality of holes PEc are formed by the anodic oxidation method (or the anodization method) carried out so that the second applied voltage V2 at the end time is lower than the first applied voltage V1 at the start time (V1>V2). In other words, in the electric conduction initial stage, the electric conduction is carried out at the predetermined first voltage value V1, and in the electric conduction end stage, the electric conduction is carried out at the predetermined second voltage value V2 lower than the first voltage value V1 so that the partition wall thickness between the holes PEc adjacent to each other is smaller on the bottom side of the holes PEc than that on the main surface side. In one example, the electric conduction is carried out with a DC voltage for 0.5 hours (30 minutes) so that the DC voltage is linearly changed from 60 V to 20 V over time (V1=60 V, V2=20 V, −80 V/h (≈−1.333 V/min)). Thereby, for example, as shown in FIG. 16C, the plurality of holes PEc are further formed so as to further extend in the direction Dz continuously to the respective plurality of holes PEb formed in the first hole formation step, and the partition wall thickness between the holes PEc adjacent to each other becomes relatively larger on the main surface side, and relatively smaller on the bottom side. Thereby, the plurality of holes PEc are formed, the plurality of holes PEc having the partition wall thickness between the holes PEc adjacent to each other of about 120 nm on the main surface side, and about 40 nm on the bottom side. An average distance between centers in the holes PEc adjacent to each other is about 150 nm on the main surface side, and about 50 nm on the bottom side. A thickness of a hole group layer 139 with the above-described plurality of holes PEc formed is about 3 μm. A thickness of an alumina layer in bottom portions of the holes PEc in this case is about 20 nm. These holes PEc extend and are formed in the direction crossing the main surface while branching by the partition wall thickness changing.

Next, by immersing the metal substrate 13 in the etching liquid, the recesses 140 in which part of the partition walls between the plurality of holes PEb are left are formed in the metal substrate 13 corresponding to the first regions AR1 defined in the region definition step (the partition-wall partially leaving/removing step, FIG. 14). More specifically, the metal substrate 13 after the second hole formation step is immersed in phosphoric acid liquid (the etching liquid) of 8 vol %, and is left for 150 minutes. In the present embodiment, since the partition wall thickness of the hole group layer 139 is smaller than the partition wall thickness of the hole group layer 138, the hole group layer 139 is dissolved and removed dominantly to the hole group layer 138. Therefore, as shown in FIG. 14, by the etching for 150 minutes, aluminum oxide (alumina) forming the hole group layer 139 disappears, aluminum oxide forming the hole group layer 138 disappears with the partition walls 1401 in the predetermined range left, and the slit groove-like recesses 140 where the part of the partition walls 1401 between the plurality of holes PEb are left in the predetermined range can be formed. While the situation is similar to the foregoing situation, in one example, the predetermined range is within a range of about 25 μm to about 55 μm from the main surface in the direction Dz.

The resist layer 133 left in each of the second regions AR2 is then removed (a resist layer removal step).

Through the above-described manufacturing steps, the hole group layer 138 of the second regions AR protected and left by the resist layer 133 in the partition-wall partially leaving/removing step becomes the X-ray absorption portions 111c (or the X-ray phase portions) of the grating 11c, the recesses 140 with the part of the partition walls 1401 in the first regions AR left become the X-ray transmission portions 112c of the grating 11c, and the left part of the partition walls 1401 become the porous members 1121c, so that the metal grating for X-ray 1c having the configuration shown in FIG. 13 is manufactured. The metal grating for X-ray 1c may be configured such that the resist layer 133 is not removed (the resist layer removal step is omitted) to serve as the protective layer 15 that protects top portions of the X-ray absorption portions 111c, as indicated by broken line in FIG. 13.

As described above, the third method for manufacturing the high aspect ratio structure in which, as one example, the metal grating for X-ray 1c is manufactured exerts actions and effects similar to those of the first method for manufacturing the high aspect ratio structure, in which the metal grating for X-ray 1a in the first embodiment is manufactured.

In the third method for manufacturing the high aspect ratio structure, since the hole formation step is divided into the first and second hole formation steps, in the base portions 1112c in the hole group layer 138 of the second regions AR protected by the resist layer 133 and left in the partition-wall partially leaving/removing step, that is, the X-ray absorption portions 111c of projections formed between the recesses 140 adjacent to each other in the partition-wall partially leaving/removing step, the plurality of holes PEb are not formed, so that the X-ray absorption portions 111c of the projections can be more firmly supported.

While in the third method for manufacturing the foregoing metal grating for X-ray 1c, the second and first regions AR2, AR1 are defined by presence or absence of the resist layer 133 (15) as in the first embodiment, they may be defined by presence or absence of closing of the plurality of holes PEb in place of the resist layer 133 (15) as in the second embodiment.

Moreover, in the third method for manufacturing the foregoing metal grating for X-ray 1c, the first hole formation step may be the partition-wall thinning hole formation step. That is, in the first hole formation step, the plurality holes may be formed by the anodic oxidation method or the anodization method while controlling the voltage. More specifically, similar to the first embodiment, in this first hole formation step, the plurality of holes are formed by the anodic oxidation method or the anodization method carried out so that the second applied voltage V2 at the end time is lower than the first applied voltage V1 at the start time (V1>V2). In one example, the electric conduction is carried out with a DC voltage for 17 hours so that the DC voltage is linearly changed from 60 V to 40 V over time (V1=60 V, V2=40 V, about −1.18 V/h). Thereby, the partition wall thickness between the holes adjacent to each other becomes relatively larger on the main surface side, and relatively smaller on the bottom side. This allows the plurality of holes to be formed, the plurality of holes having the partition wall thickness between the holes adjacent to each other of about 85 nm on the main surface side, and about 80 nm on the bottom side. An average distance between centers in the holes adjacent to each other is about 150 nm on the main surface side, and about 100 nm on the bottom side. The thickness of the hole group layer with the above-described plurality of holes formed is about 110 In the second hole formation step of the partition-wall thinning hole formation step in this case, as one example, the electric conduction is carried out with a DC voltage for 0.5 hours so that the DC voltage is linearly changed from 40 V to 20 V over time (V1=40 V, V2=20 V, −40 V/h (≈−0.667 V/min)). Thereby, for example, the plurality of holes are further formed so as to further extend in the direction Dz continuously to the respective plurality of holes formed in the first hole formation step, and the partition wall thickness between the holes adjacent to each other becomes relatively larger on the main surface side, and relatively smaller on the bottom side. This allows the plurality of holes to be formed, the plurality of holes having the partition wall thickness between the holes adjacent to each other of about 80 nm on the main surface side, and about 40 nm on the bottom side. An average distance between centers in the holes adjacent to each other is about 100 nm on the main surface side, and about 50 nm on the bottom side. The thickness of the hole group layer with the above-described plurality of holes formed is about 2 μm. The thickness of the alumina layer in the bottom portions of the holes in this case is about 20 nm.

Moreover, in the third method for manufacturing the foregoing metal grating for X-ray 1c, the first hole formation step is the partition-wall thinning hole formation step, and in the second hole formation step, the plurality of holes are further formed so as to further extend in the direction continuously to the respective plurality of holes formed in the first hole formation step. Preferably, in this case, in the second hole formation step, the plurality of holes are formed by the anodic oxidation method or the anodization method carried out at an applied voltage of the constant value from the start time to the end time. In one example, as in the first embodiment, in the first hole formation step, the electric conduction is carried out with a DC voltage for 20 hours so that the DC voltage is linearly changed from 60 V to 20 V, and the plurality of holes are formed as in the first embodiment. In the second hole formation step in this case, the electric conduction is carried out at a constant voltage 20 V for one hour from the start time to the end time. This allows the plurality of holes to be formed, the plurality of holes having the partition wall thickness between the holes adjacent to each other of about 40 nm from the main surface side to the bottom side. An average distance between centers in the holes adjacent to each other is about 50 nm regardless of the thickness in the thickness direction (the direction Dz) of the metal substrate 13. The thickness of the hole group layer with the above-described plurality of holes formed is about 2 μm. The thickness of the alumina layer in the bottom portions of the holes in this case is about 20 nm.

Next, another embodiment will be described.

Fourth Embodiment; a Metal Grating for X-Ray, and a Method for Manufacturing the Same as One Example of a High Aspect Ratio Structure While in the metal grating for X-rays 1a, 1b, 1c in the foregoing first to third embodiments, the plurality of recesses 134, 137, 140, which are slit groove-like spaces, function as the X-ray transmission portions 112a, 112b, 112c, respectively, and the plurality of plate-like (layered) hole group layers 132, 136, 138 left by the formation of the plurality of recesses 134, 137, 140 function as the X-ray absorption portions (or the X-ray phase portions) 111a, 111b, 111c, respectively, an X-ray absorbent material capable of absorbing X-rays may be buried into the respective plurality of recesses 134, 137, 140, by which the plurality of recesses 134, 137, 140 in which this X-ray absorption material is buried function similar to the X-ray absorption portions (or the X-ray phase portions) 111a, 111b, 111c, respectively, and the plurality of plate-like (layered) hole layers 132, 136, 138 left by the formation of the plurality of recesses 134, 137, 140 may function similar to the X-ray transmission portions 112a, 112b, 112c, respectively.

Figure 17:
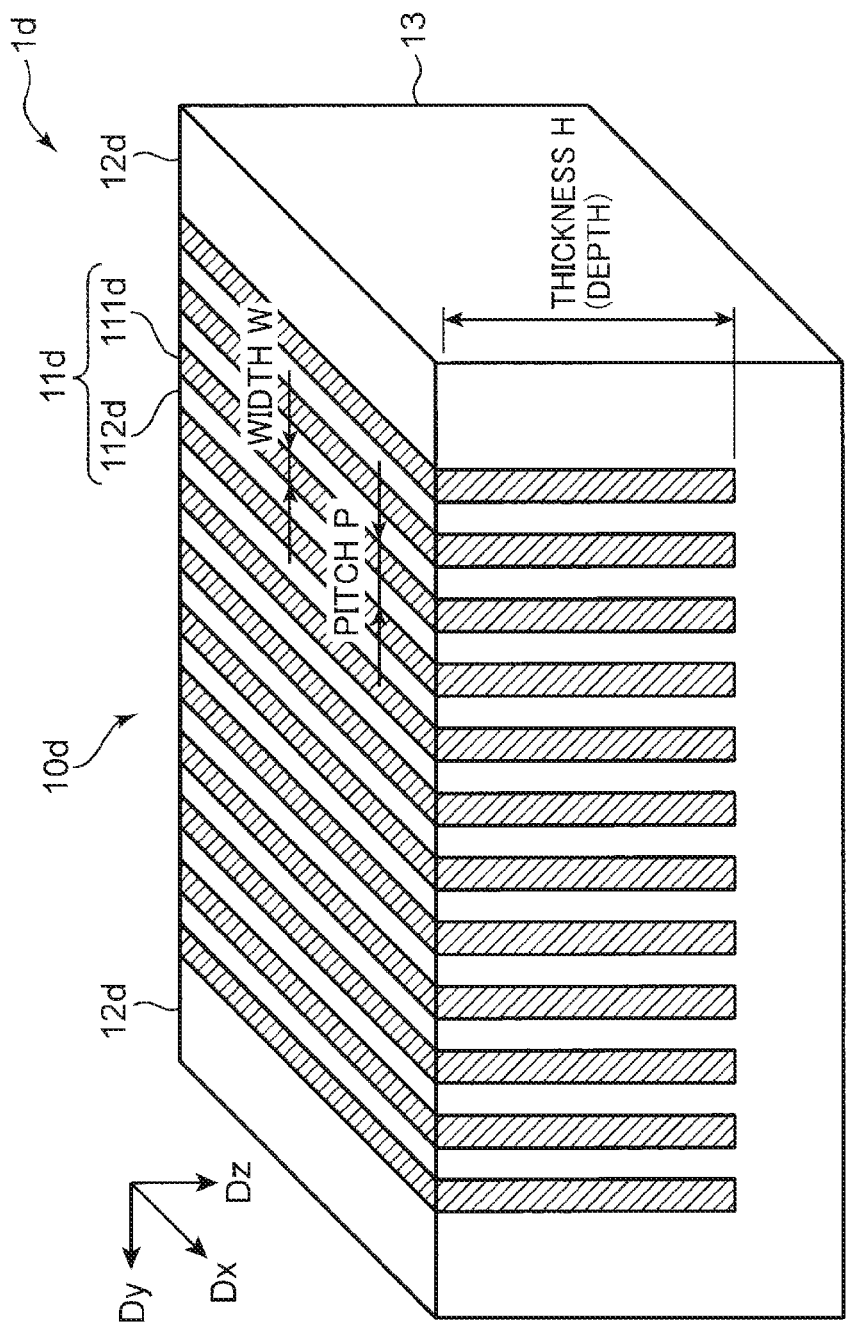
FIG. 17 is a view for describing a configuration of a metal grating for X-ray according to a fourth embodiment.
Figure 18:
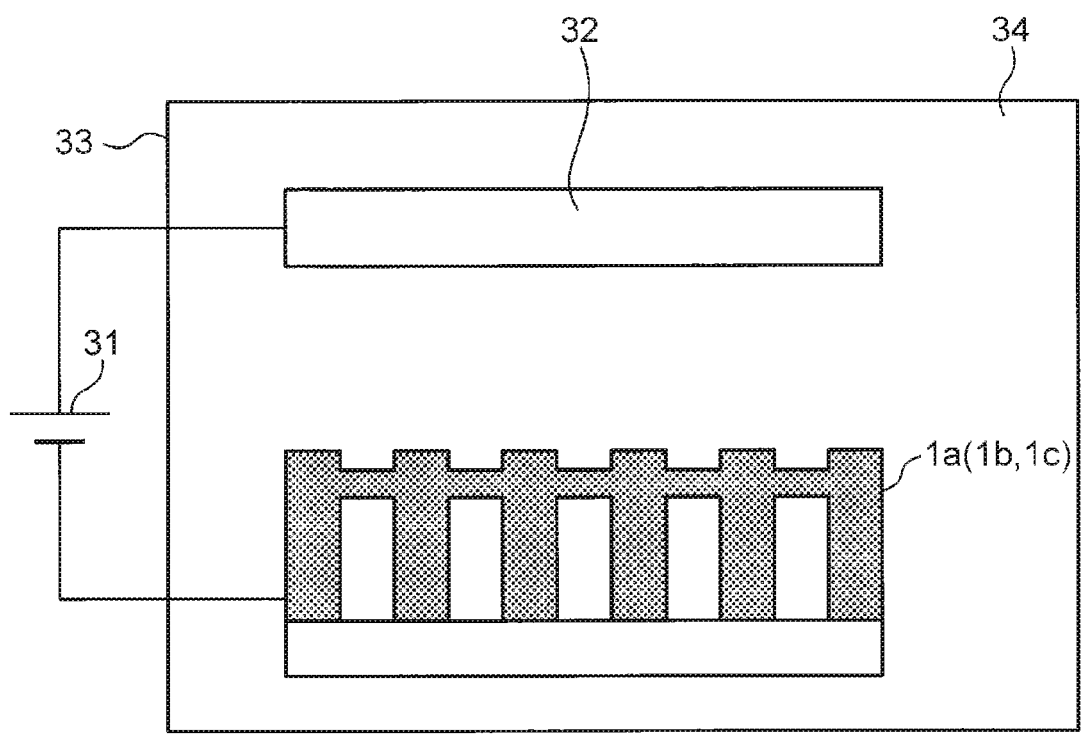
FIG. 18 is a view for describing electroforming for burying recesses with a metal material.

For such a metal grating for X-ray 1d of a fourth embodiment, one example of the metal grating for X-ray 1d, in which the X-ray absorbent material capable of absorbing X-rays is buried in the respective plurality of recesses 134, 137, 140 is shown in FIG. 17. FIG. 17 is a view for describing a configuration of the metal grating for X-ray according to the fourth embodiment. In FIG. 17, illustration of a porous member included in a part of an inside of each X-ray absorption portion 111d is omitted. Here, while the metal grating for X-ray 1d is a modification to the metal grating for X-ray 1a of the first embodiment, the metal grating for X-ray 1d (not shown) of a modification to each of the metal gratings for X-ray 1b, 1c of the second and third embodiments can also be similarly described and configured. FIG. 18 is a view for describing electroforming for burying recesses with a metal material.

The metal grating for X-ray 1d in the fourth embodiment includes a grating region 10d and a frame region 12d provided in the metal substrate 13, as shown in FIG. 17. The grating region 10d is a region where the grating 11d is formed, and the grating 11d includes a plurality of X-ray absorption portions 111d and a plurality of X-ray transmission portions 112d. The frame region 12d in the metal grating for X-ray 1d of the fourth embodiment is similar to the frame region 12a in the metal grating for X-ray 1a of the first embodiment, and thus, description thereof is omitted.

In the metal grating for X-ray 1a in the first embodiment, the X-ray absorption portions 111a are plate-like (layered) members (in the forgoing, the hole group layer 132) along the surface DxDz, made from the metal substrate 13 by carrying out the foregoing respective steps, while the X-ray transmission portions 112a are plate-like (layered) spaces (slit grooves) (in the foregoing, the recesses 134) along the surface DxDz, made from the metal substrate 13 by carrying out the foregoing respective steps. On the other hand, in the metal grating for X-ray 1d in the fourth embodiment, the X-ray absorption portions 111d are members made of a metal material having X-ray absorbency (preferably, comparatively high X-ray absorbency), the metal material being put into the plate (layered) spaces (the slit grooves) along the surface DxDz made from the metal substrate 13 by carrying out respective steps described later, and the X-ray transmission portions 112d are plate-like (layered) members along the surface DxDz made from the metal substrate 13 by carrying out the respective steps described later. With this exception, the grating region 10d with the grating 11d formed in the metal grating for X-ray 1d of the fourth embodiment is similar to the grating region 10a with the grating 11a formed in the metal grating for X-ray 1a of the first embodiment, and thus, description thereof is omitted.

The above-described metal grating for X-ray 1d is manufactured by further including an X-ray absorbent material burying step of burying the X-ray absorbent material capable of absorbing X-rays in recesses after the foregoing hole formation step, region formation step, and partition-wall partially leaving/removing step described in the first embodiment.

In order to manufacture the metal grating for X-ray 1d in the fourth embodiment, respective steps similar to the foregoing hole formation step configured by the partition-wall thinning hole formation step itself (the protective film formation step, the anodic oxidation step), region definition step (the resist layer formation step, the patterning step), and partition-wall partially leaving/removing step for manufacturing the metal grating for X-ray 1a in the first embodiment are carried out. The resist layer removal step may be carried out after the partition-wall partially leaving/removing step.

After the partition-wall partially leaving/removing step, a second metal (including an alloy) having a second property different from a first property to X-rays in a first metal (including an alloy. In the foregoing example, aluminum) forming the metal substrate 13 is buried in the slit groove-like recesses 134 where the part of the partition walls 1341 between the plurality of holes PEa are left in the predetermined range (a metal burying step (here, the X-ray absorbent material burying step)). The second metal is, for example, a metal of an element having a comparatively heavy atomic weight, or a noble metal, more specifically, for example, gold (Au), platinum (Pt), rhodium (Rh), ruthenium (Ru), iridium (Ir) or the like.

More specifically, the second metal is buried in the respective plurality of recesses 134 by the electroforming (an electroplating method). Especially, in the foregoing, since side walls of the recesses 134 are made of electrically insulating aluminum dioxide (alumina), and on the other hand, bottom portions thereof are made of electrically conductive aluminum, the second metal can be buried in the recesses 134 by bottom-up from the bottom portions. More particularly, as shown in FIG. 18, a cathode of a power supply 31 is connected to the metal substrate 13 (here, the metal grating for X-ray 1a) after the partition-wall partially leaving/removing step, and an anodic electrode 32 connected to an anode of the power supply 31, and the metal substrate 13 (here, the metal grating for X-ray 1a) are immersed in a plating liquid 34 inside a tank 33 where the plating liquid 34 is stored. An insulating film is formed in side surfaces and the like of the metal substrate 13 so as not to plate the side surfaces and the like of the metal substrate 13, and the insulating film at a portion connected to the cathode of the power supply 31 is removed, so that at this removal portion, the cathode of the power supply 31 and the metal substrate 13 are electrically connected to each other. This allows the second metal to be deposited and grow from the bottom side of the respective plurality of recesses 134 by the electroforming. When this second metal buries the respective plurality of recesses 134, the electroforming is ended. This allows the second metal to bury the respective plurality of recesses 134, and grow by the depth (the thickness H) of the recesses 134. In this manner, the X-ray absorption portions 111d are formed.

Through the above-described manufacturing steps, the metal grating for X-ray 1d having the configuration shown in FIG. 17 is manufactured, the metal grating for X-ray 1d having the X-ray absorption portions 111d made of the second metal as the X-ray absorbent material buried in the respective plurality of recesses 134, and the X-ray transmission portions 112d including the hole group layer 132.

As described above, the fourth method for manufacturing the high aspect ratio structure in which, as one example, the metal grating for X-ray 1d is manufactured, exerts actions and effects similar to those of the first method for manufacturing the high aspect ratio structure, in which the metal grating for X-ray 1a in the first embodiment is manufactured.

In the fourth method for manufacturing the high aspect ratio structure, burying the X-ray absorbent material in the recesses 134 enables the first regions AR1 to be formed as the X-ray absorption portions 111d, and the second regions AR2 to be formed as the X-ray transmission portions 112d.

Here, as described above, in the case where the metal is buried in the respective plurality of recesses 134 by the electroforming (the electroplating method), there is a risk that a space (a void, a portion that is not filled with the metal) occurs inside the buried metal portion. However, in the case where the metal grating for X-ray 1d in the fourth embodiment is manufactured using the metal grating for X-ray 1c in the third embodiment, since in the metal grating for X-ray 1c in the third embodiment, the second hole formation step is carried out, a surface area of the bottom portion of each of the recesses 140 is larger than that in the case of only the first hole formation step, and the surface area where a current can flow in the bottom portion of the recess 140 is larger than that in the case of only the first hole formation step. Therefore, since the metal effectively grows from the bottom portions of the recesses 140 by the electroforming, the occurrence of a void can be effectively suppressed. As a result, in the metal grating for X-ray 1d of the fourth embodiment using the metal grating for X-ray 1c of the third embodiment, the X-ray absorption portions 111d can be more elaborately formed by the electroforming.

While in the foregoing, the first metal is a metal (including an alloy) having X-ray transmissivity as the first property, and the second metal is a metal (including an alloy) having X-ray absorbency as the second property, the first metal may be a metal (including an alloy) having a low phase shift property that phase shift is small as the first property, and the second metal may be a metal (including an alloy) having a high phase shift property that the phase shift is relatively large (a higher phase shift than the phase shift of the first metal) as the second property.

Moreover, in the case where the metal is buried in the recesses 134 by the electroforming, in order to increase the transmittance, the other main surface in the metal substrate 13 may be polished until the bottoms of the recesses 134, that is, the buried metal is exposed. Moreover, in this case, a plate-like member of a material having a high transmittance (e.g., acrylic resin or the like) may be bonded to the grating 11 as a support substrate with an adhesive or the like.

Moreover, while in the foregoing first to fourth embodiments, the metal grating for X-ray 1 (1a, 1b, 1c, 1d) has a one-dimensional periodic structure, the present invention is not limited thereto. The metal grating for X-ray 1 may be a grating having, for example, a two-dimensional periodic structure. For example, as to a metal for X-ray having the two-dimensional periodic structure, dots, which each make up a member of the two-dimensional periodic structure, are arranged at equal intervals at a predetermined distance from each other in linear independent two directions to be configured. The metal grating for X-ray having the above-described two-dimensional periodic structure can be formed by boring holes of a high aspect ratio in a plane in a two-dimensional period, or by erecting circular columns of a high aspect ratio in a plane in a two-dimensional period. Alternatively, the metal may be buried in these spaces similar to the foregoing.

Moreover, while in the foregoing first to fourth embodiments, aluminum is used as the metal (including an alloy) in which the plurality of holes can be formed by the anodic oxidation method or the anodization method, the metal substrate 13 may be formed of another metal (including an alloy). As the above-described metal, for example, apart from the foregoing aluminum (Al), tungsten (W), molybdenum (Mo), silicon (Si), gallium arsenide (GaAs), and indium phosphide (InP) are cited. In these metals, minute vertical holes are easily formed by the anodic oxidation method or the anodization method. In the case where treatment similar to the anodic oxidation method is carried out, the metal substrate 13 may not oxidize, depending on the material of the metal substrate 13, and in this case, the treatment is not referred to as the anodic oxidation method, but referred to as the anodization method.

In the case where the metal substrate 13 is formed of tungsten or molybdenum, the plurality of holes can be formed by the anodic oxidation method using a solution of nitride acid, oxalic acid, or the like.

In the case where the metal substrate 13 is formed of silicon, for example, if the metal substrate 13 is a p-type silicon (001) substrate, the plurality of holes can be formed by the anodization method using a mixed solution of hydrofluoric acid and methanol.

In the case where the metal substrate 13 is formed of gallium arsenide or indium phosphide, for example, if the metal substrate 13 is an n-type gallium arsenide (001) substrate, the plurality of holes can be formed by the anodization method using an ammonium hydroxide solution ($NH_4OH$). In this anodization method, the metal substrate 13 is immersed in an ammonium hydroxide solution while being subjected to photoirradiation and magnetic field application, and a voltage is applied.

In the case where this metal substrate 13 is formed of any of tungsten (W), molybdenum (Mo), silicon (Si), gallium arsenide (GaAs), and indium phosphide (InP), the hole-sealing treatment is carried out by subjecting the metal substrate 13 to heating treatment in an oxygen atmosphere. This allows the holes PE to be sealed by volume expansion by oxidation.

Moreover, while in the foregoing first to fourth embodiments, by beforehand forming the protective film 131 made of the quartz film in the other main surface, the hole group layer 132 by the anodic oxidation method or the anodization method is formed only in the one main surface, in order to suppress change of surface accuracy by the oxidation, the hole group layers 132 may be formed in both the one and the other main surfaces. In this case, after the hole group layers 132 are formed in both the surfaces, for example, a dry resist film may be pasted onto the surface that is not patterned, or for example, the quartz film may be formed by a technique such as TEOS-CVD and the like, by which the protective film may be formed.

Next, another embodiment will be described.

Fifth and Sixth Embodiments; a Talbot Interferometer and a Talbot-Lau Interferometer Since in the metal grating for X-ray 1 (1*a*, 1*b*, 1*c*, 1*d*) of the above-described embodiments, the metal portion can be formed at the high aspect ratio, the metal grating for X-ray 1 can be preferably used for the Talbot interferometer and the Talbot-Lau interferometer for X-ray. These Talbot interferometer for X-ray and Talbot-Lau interferometer for X-ray using a metal grating DG will be described.

Figure 19:
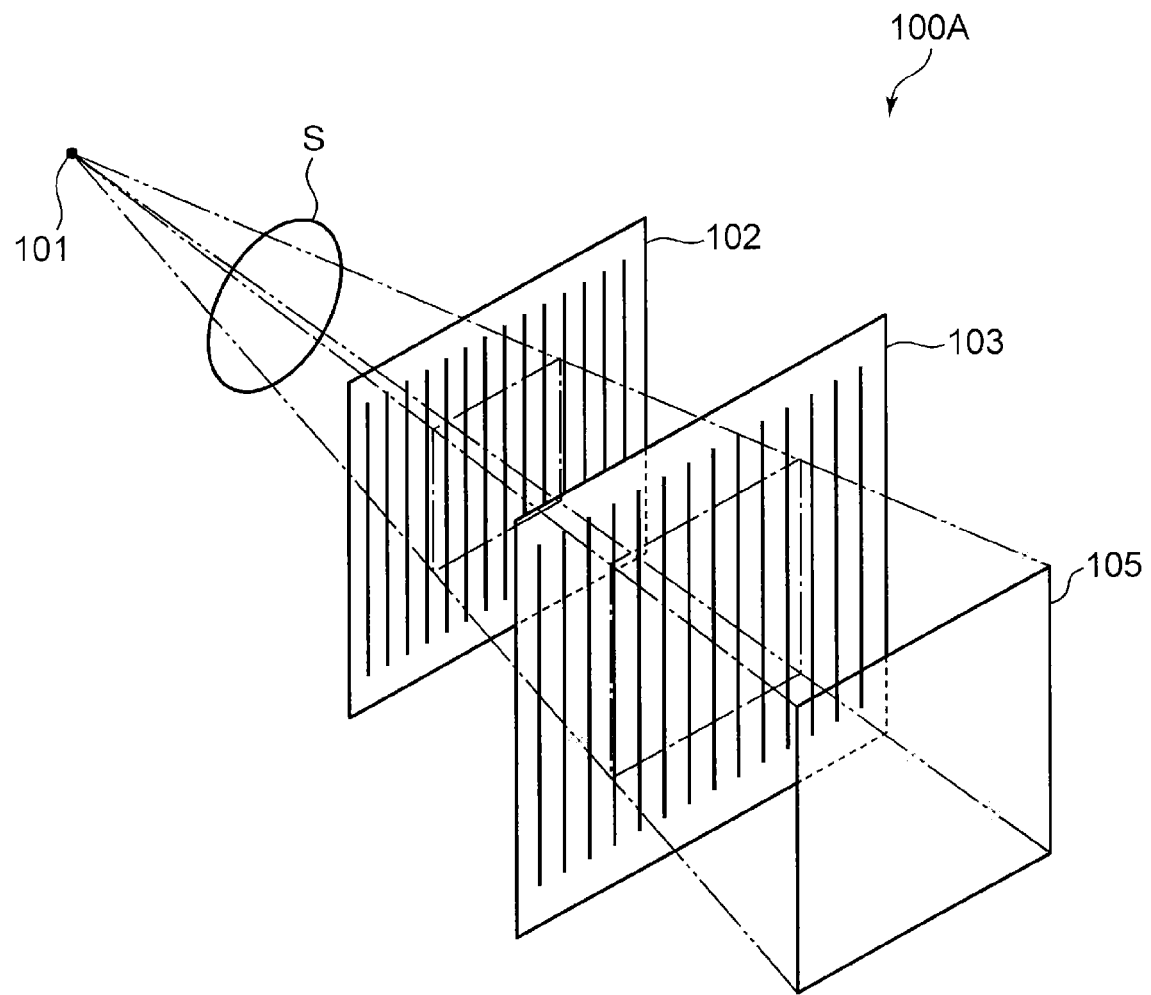
FIG. 19 is a perspective view showing a configuration of a Talbot interferometer for X-ray according to a fifth embodiment.
Figure 20:
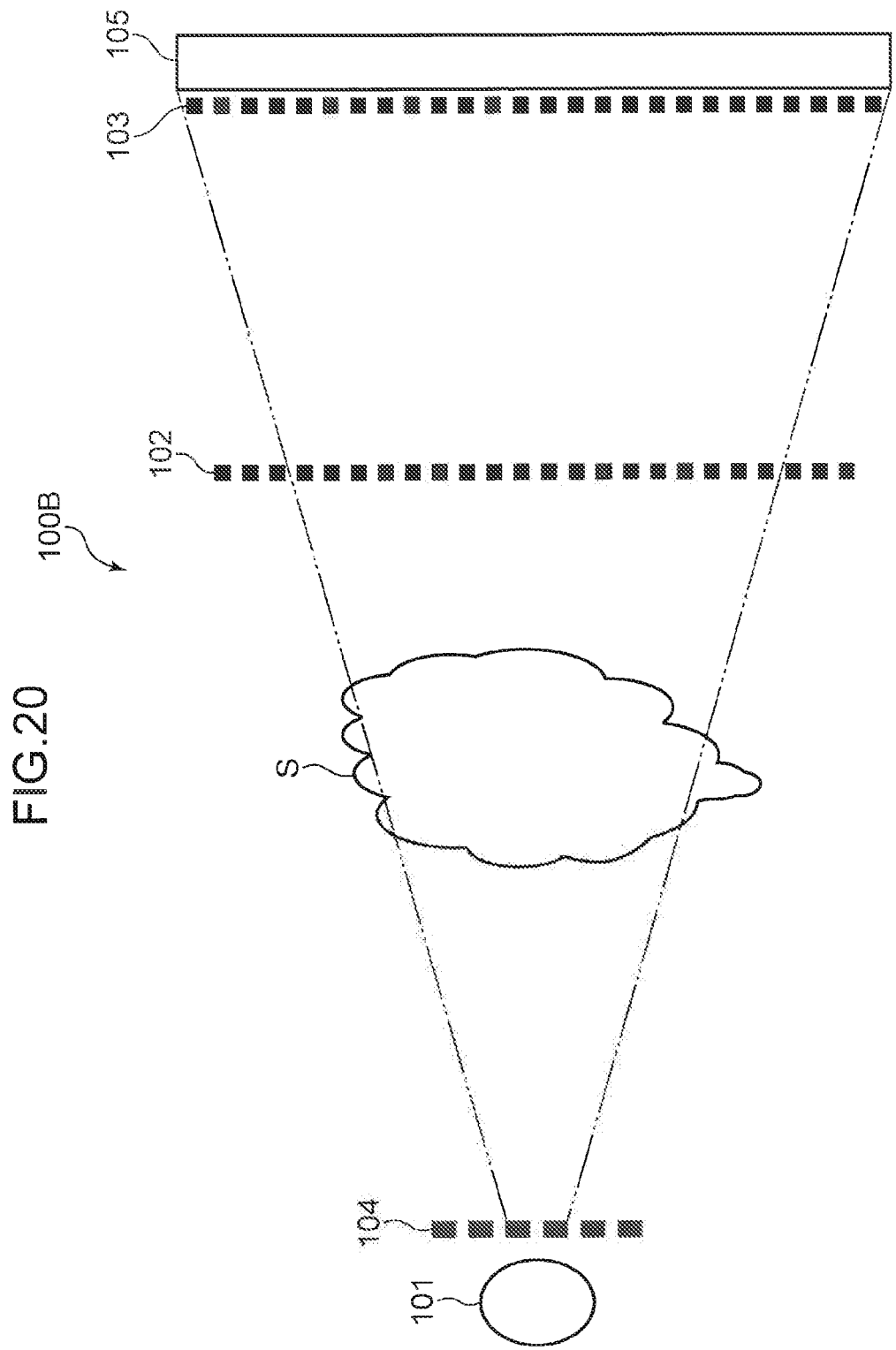
FIG. 20 is a top view showing a configuration of a Talbot-Lau interferometer for X-ray according to a sixth embodiment.

FIG. 19 is a perspective view showing a configuration of a Talbot interferometer for X-ray in a fifth embodiment. FIG. 20 is a top view showing a configuration of a Talbot-Lau interferometer for X-ray in a sixth embodiment.

As shown in FIG. 19, a Talbot interferometer for X-ray 100A of the embodiment includes an X-ray source 101 configured to radiate X-rays of a predetermined wavelength, a phase type first diffraction grating 102 configured to diffract the X-rays radiated from the X-ray source 101, and an amplitude type second diffraction grating 103 configured to diffract the X-rays diffracted by the first diffraction grating 102 to thereby form an image contrast, and the first and second diffraction gratings 102, 103 are set to a condition for configuring the X-ray Talbot interferometer. The X-rays that generate the image contrast in the second diffraction grating 103 are detected, for example, by an X-ray image detector 105 configured to detect the X-rays. In this Talbot interferometer for X-ray 100A, at least one of the first diffraction grating 102 and the second diffraction grating 103 is the metal grating for X-ray 1 manufactured by any of the foregoing methods for manufacturing the metal grating for X-ray 1.

The condition for configuring the Talbot interferometer 100A is represented by the following expressions (1) and (2). Expression (2) is premised that the first diffraction grating 102 is the phase type diffraction grating.

$$l = \lambda(a/(L+Z1+Z2)) \quad (1)$$

$$Z1 = (m+\tfrac{1}{2}) \times (d^2/\lambda) \quad (2)$$

Here, l is a coherence length, $\lambda$ is a wavelength of the X-rays (normally, a center wavelength), a is an opening size of the X-ray source 101 in a direction almost perpendicular to diffraction members of the diffraction gratings, L is a distance from the X-ray source 101 to the first diffraction grating 102, Z1 is a distance from the first diffraction grating 102 to the second diffraction grating 103, Z2 is a distance from the second diffraction grating 103 to the X-ray image detector 105, m is an integer, d is a period of the diffraction members (a period of the diffraction gratings, a grating constant, a distance between the centers of the adjacent diffraction members, the pitch P).

In the Talbot interferometer for X-ray 100A having the above-described configuration, the X-rays are radiated from the X-ray source 101 to the first diffraction grating 102. These radiated X-rays generate a Talbot effect, and form a Talbot image in the first diffraction grating 102. This Talbot image receives an action in the second diffraction grating 103, and forms the image contrast of moire fringes. This image contrast is then detected in the X-ray image detector 105.

The Talbot effect indicates that when light enters the diffraction grating, the same image as that in the diffraction grating (a self-portrait of the diffraction grating) is formed at a certain distance, and this distance is referred to as a Talbot distance L, and this self-portrait is referred to as a Talbot image. In the case where the diffraction grating is the phase type diffraction grating, the Talbot distance L becomes Z1 represented in expression (2) (L=Z1). As to the Talbot image, at odd-number times of L (=(2 m+1) where L and m are integers), an inverted image appears, and at even-number times of L (=2 mL), a normal image appears.

Here, when a subject S is disposed between the X-ray source 101 and the first diffraction grating 102, the moire fringes are modulated by the subject S, and a modulation amount thereof is proportional to an angle at which the X-rays are bent by a refraction effect by the subject S. Therefore, analyzing the moire fringes allows a structure of the subject S and an inside thereof to be detected.

In the Talbot interferometer 100A having the above-described configuration in FIG. 19, the X-ray source 101 is a single point light source, this single light source can be configured by further including a single slit plate formed with a single slit, and the X-rays radiated from the X-ray source 101 pass through the single slit of the single slit plate and are radiated toward the first diffraction grating 102 through the subject S. The slit is an elongated rectangular opening extending in one direction.

On the other hand, as shown in FIG. 20, a Talbot-Lau interferometer 100B includes the X-ray source 101, a multislit plate 104, the first diffraction grating 102, and the second diffraction grating 103. That is, the Talbot-Lau interferometer 100B further includes the multislit plate 104 where a plurality slits are formed in parallel on an X-ray radiation side of the X-ray source 101 in addition to the Talbot interferometer 100A shown in FIG. 19.

This multislit plate 104 is a so-called 0-th grating, and may be the metal grating for X-ray 1 manufactured by any of the foregoing methods for manufacturing the metal grating for X-ray 1. Since by manufacturing the multislit plate 104 by any of the foregoing methods for manufacturing the metal grating for X-ray 1, X-rays can be transmitted through the slit-like X-ray transmission portions 112 (112*a*, 112*b*, 112*c*, 112*d*), and can be more surely blocked by the slit-like X-ray absorption portions 111 (111*a*, 111*b*, 111*c*, 111*d*), the transmission and non-transmission of the X-rays can be clearly distinguished, so that the multislit plate 104 enables the X-rays radiated from the X-ray source 101 to surely serve as a multi-light source.

Changing to the Talbot-Lau interferometer 100B increases an X-ray amount radiated toward the first diffraction grating 102 through the subject S, as compared with the Talbot interferometer 100A, and thus, more favorable moire fringes can be obtained.

Next, another embodiment will be described.

Seventh Embodiment; an X-Ray Imaging Apparatus

While the metal grating for X-ray 1 (1*a*, 1*b*, 1*c*, 1*d*) can be utilized for various optical apparatuses, for example, it can be preferably used for an X-ray imaging apparatus because the X-ray absorption portions 111 (111*a*, 111*b*, 111*c*, 111*d*) can be formed at the high aspect ratio. Especially, the X-ray imaging apparatus using the X-ray Talbot interferometer is one of phase contrast techniques, in which an X-ray is treated as a wave, and a phase shift of the X-ray caused by passing through a subject is detected to thereby obtain an transmission image of the subject, and there is an advantage that as compared with an absorption contrast technique of obtaining an image in which a magnitude of the X-ray absorption by the subject is used as contrast, about 1000 times as large sensitivity improvement can be expected, by which an X-ray irradiation amount can be reduced, for example, to $\tfrac{1}{100}$ to $\tfrac{1}{1000}$. In the present embodiment, the X-ray imaging apparatus including the X-ray Talbot interferometer using the metal grating for X-ray 1 will be described.

Figure 21:
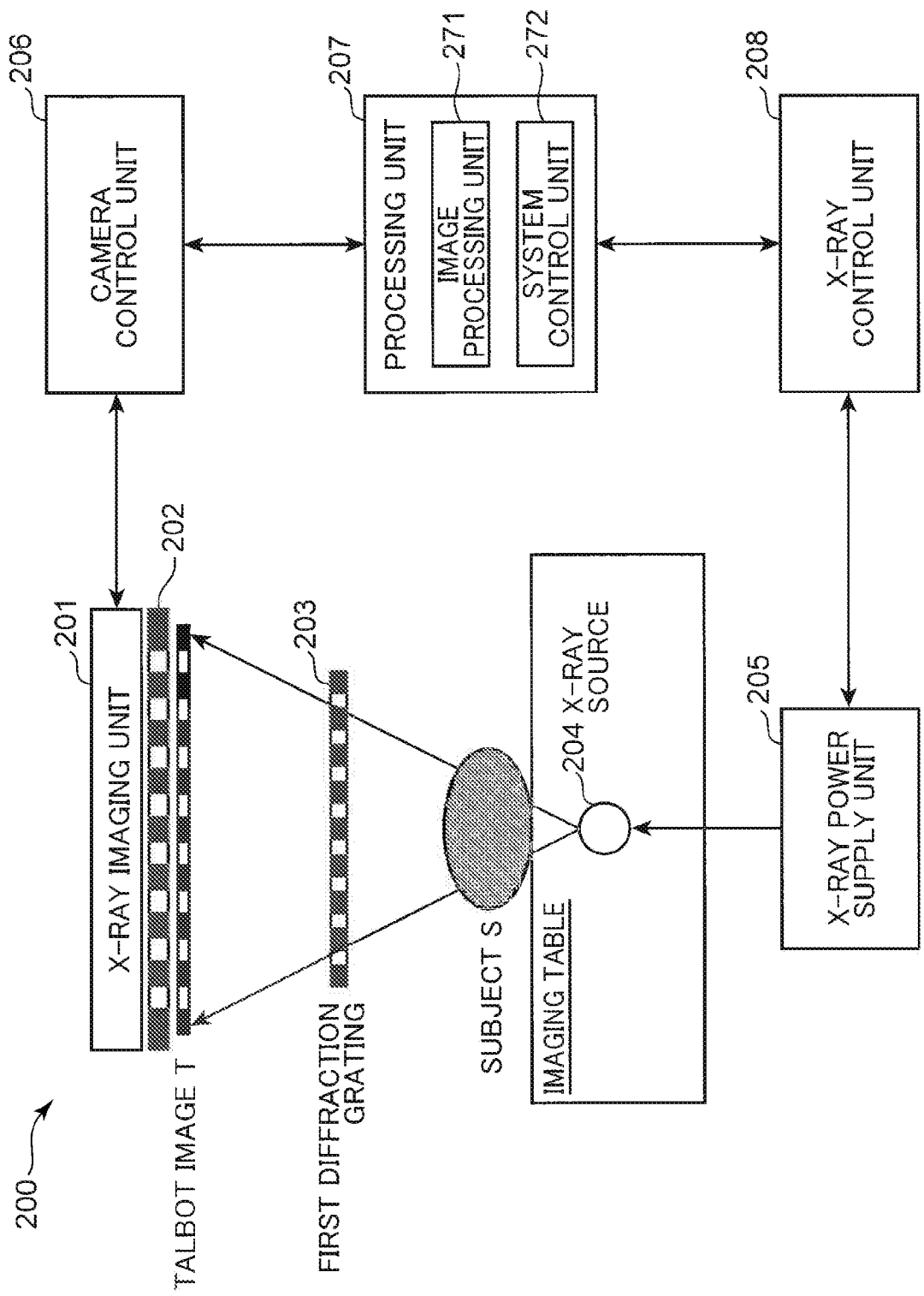
FIG. 21 is an explanatory view showing a configuration of an X-ray imaging apparatus according to a seventh embodiment.

FIG. 21 is an explanatory view showing a configuration of an X-ray imaging apparatus in a seventh embodiment. In FIG. 21, an X-ray imaging apparatus 200 includes an X-ray imaging unit 201, a second diffraction grating 202, a first diffraction grating 203, and an X-ray source 204, and in the present embodiment, further includes an X-ray power supply unit 205 configured to supply power to the X-ray source 204, a camera control unit 206 configured to control imaging operation of the X-ray imaging unit 201, a processing unit 207 configured to control the whole operation of the present X-ray imaging apparatus 200, and an X-ray control unit 208 configured to control radiation operation of X-rays in the X-ray source 204 by controlling power supply operation of the X-ray power supply unit 205.

The X-ray source 204 is, for example, an apparatus configured to radiate X-rays, and irradiate the first diffraction grating 203 with the X-rays by power fed from the X-ray power supply unit 205. The X-ray source 204 is an apparatus configured to apply a high voltage supplied from the X-ray power supply unit 205 to a section between a cathode and an anode and cause electrons emitted from a filament of the cathode to collide with the anode, by which the X-rays are radiated.

The first diffraction grating 203 is a diffraction grating configured to generate the Talbot effect by the X-rays radiated from the X-ray source 204. The first diffraction grating 203 is, for example, the diffraction grating manufactured by any of the foregoing methods for manufacturing the metal grating for X-ray 1. The first diffraction grating 203 is configured to satisfy the condition for generating the Talbot effect, and is a grating sufficiently coarser than a wavelength of the X-rays radiated from the X-ray source 204, for example, a phase type diffraction grating having the grating constant (the period of the diffraction grating) d of about 20 times or more of the wavelength of the relevant X-rays. The first diffraction grating 203 may be such an amplitude type diffraction grating.

The second diffraction grating 202 is a transmission type amplitude type diffraction grating, which is disposed at a position substantially at the Talbot distance L from the first diffraction grating 203 to diffract the X-rays diffracted by the first diffraction grating 203. Similar to the first diffraction grating 203, the second diffraction grating 202 is also, for example, the diffraction grating manufactured by any of the foregoing methods for manufacturing the metal grating for X-ray 1.

These first and second diffraction gratings 203, 202 are set to the condition for configuring the Talbot interferometer, the condition being represented by the foregoing expressions 1 and 2.

The X-ray imaging unit 201 is an apparatus configured to capture an image of the X-rays diffracted by the second diffraction grating 202. The X-ray imaging unit 201 is, for example, a flat panel detector (FPD), an image intensifier camera or the like, the flat panel detector including a two-dimensional image sensor in which a thin film layer including a scintillator configured to absorb energy of the X-rays and emit fluorescence is formed on a light-receiving surface, and the image intensifier camera including an image intensifier unit configured to convert incident photons to electrons in a photoelectric surface, increase these electrons by a microchannel plate, and causes this increased electron group to collide with a fluorescence material and emit light, and a two-dimensional image sensor configured to image output light of the image intensifier unit.

The processing unit 207 is an apparatus configured to control the respective units of the X-ray imaging apparatus 200 to thereby control the operation of the whole X-ray imaging apparatus 200, and the processing unit 207 includes, for example, a microprocessor and peripheral circuits thereof, and functionally includes an image processing unit 271 and a system control unit 272.

The system control unit 272 controls the radiation operation of the X-rays in the X-ray source 204 through the X-ray power supply unit 205 by transmitting and receiving a control signal between the X-ray control unit 208 and the system control unit 272, and controls the imaging operation of the X-ray imaging unit 201 by transmitting and receiving a control signal between the camera control unit 206 and the system control unit 272. By the control of the system control unit 272, the X-rays are radiated toward the subject S, an image generated by this is captured by the X-ray imaging unit 201, and an image signal is input to the processing unit 207 through the camera control unit 206.

The image processing unit 271 processes the generated image signal by the X-ray imaging unit 201 to generate an image of the subject S.

Next, operation of the X-ray imaging apparatus of the present embodiment will be described. The subject S is placed, for example, on an imaging table including the X-ray source 204 inside (in a back surface), by which the subject S is disposed between the X-ray source 204 and the first diffraction grating 203, and when a user (an operator) of the X-ray imaging apparatus 200 instructs imaging of the subject S through an operation unit not shown, the system control unit 272 of the processing unit 207 outputs the control signal to the X-ray control unit 208 to irradiate the subject S with the X-rays. By this control signal, the X-ray control unit 208 causes the X-ray power supply unit 205 to feed power to the X-ray source 204, so that the X-ray source 204 radiates the X-rays to irradiate the subject S with the X-rays.

The radiated X-rays pass through the first diffraction grating 203 through the subject S to be diffracted by the first diffraction grating 203, and the Talbot image T, which is a self-portrait of the first diffraction grating 203, is formed at the position at the Talbot distance L (=Z1).

This formed Talbot image T of the X-rays is diffracted by the second diffraction grating 202 to generate moire and form an image of moire fringes. This image of moire fringes is captured by the X-ray imaging unit 201 in which, for example, exposure time and the like are controlled by the system control unit 272.

The X-ray imaging unit 201 outputs the image signal of the image of the moire fringes to the processing unit 207 through the camera control unit 206. This image signal is processed by the image processing unit 271 of the processing unit 207.

Here, since the subject S is disposed between the X-ray source 204 and the first diffraction grating 203, a phase of the X-rays passing through the subject S shifts from a phase of the X-rays not passing through the subject S. Therefore, the X-rays entering the first diffraction grating 203 contain wavefront distortion, so that deformation in accordance with this occurs in the Talbot image T. Therefore, the moire fringes of the image generated by the superposition of the Talbot image T and the second diffraction grating 202 are modulated by the subject S, and this modulation amount is proportional to an angle at which the X-rays are bent by an refraction effect by the subject S. Accordingly, analyzing the moire fringes enables the structures of the subject S and the inside thereof to be detected. Moreover, imaging the subject S from a plurality of angles enables a tomographic image of the subject S to be formed by X-ray phase CT (Computed Tomography).

In the second diffraction grating 202 of the present embodiment, which is the metal grating for X-ray 1 in the foregoing embodiments including the X-ray absorption portions 111 at the high aspect ratio, favorable moire fringes can be obtained, and a high-accuracy image of the subject S can be obtained.

While in the foregoing X-ray imaging apparatus 200, the Talbot interferometer is configured by the X-ray source 204, the first diffraction grating 203, and the second diffraction grating 202, the metal grating for X-ray 1 in the foregoing embodiments as a multislit may be further disposed on the X-ray radiation side of the X-ray source 204, by which the Talbot-Lau interferometer may be configured. Configuring the above-described Talbot-Lau interferometer can increase the X-ray amount radiated to the subject S, as compared with the case of a single slit, so that more favorable moire fringes can be obtained, and a high-accuracy image of the subject S can be obtained.

Moreover, while in the foregoing X-ray imaging apparatus 200, the subject S is disposed between the X-ray source 204 and the first diffraction grating 203, the subject S may be disposed between the first diffraction grating 203 and the second diffraction grating 202.

Moreover, while in the foregoing X-ray imaging apparatus 200, the image of the X-rays is captured in the X-ray imaging unit 201, and electronic data of the image is obtained, the image may be captured with an X-ray film.

Next, another embodiment will be described.

Eighth Embodiment; an Ultrasonic Probe and a Method for Manufacturing the Same

For an ultrasonic probe used for nondestructive inspection (NDT) or for medical application, a single active element (a piezoelectric element configured to perform both sending and reception of a high-frequency acoustic wave) is generally used. In contrast, a phased-array system is configured by a probe made up of a plurality of (e.g., 16 up to 256) piezoelectric elements that can individually perform pulse oscillation, and an intensity, a phase, and the like of an ultrasonic wave emitted from each of these plurality of piezoelectric elements are individually electrically controlled, by which a propagation direction and a focus area of the ultrasonic wave can be arbitrarily changed.

Hereinafter, a method for manufacturing the ultrasonic probe for phased array as the high aspect ratio structure will be described.

Figure 22:
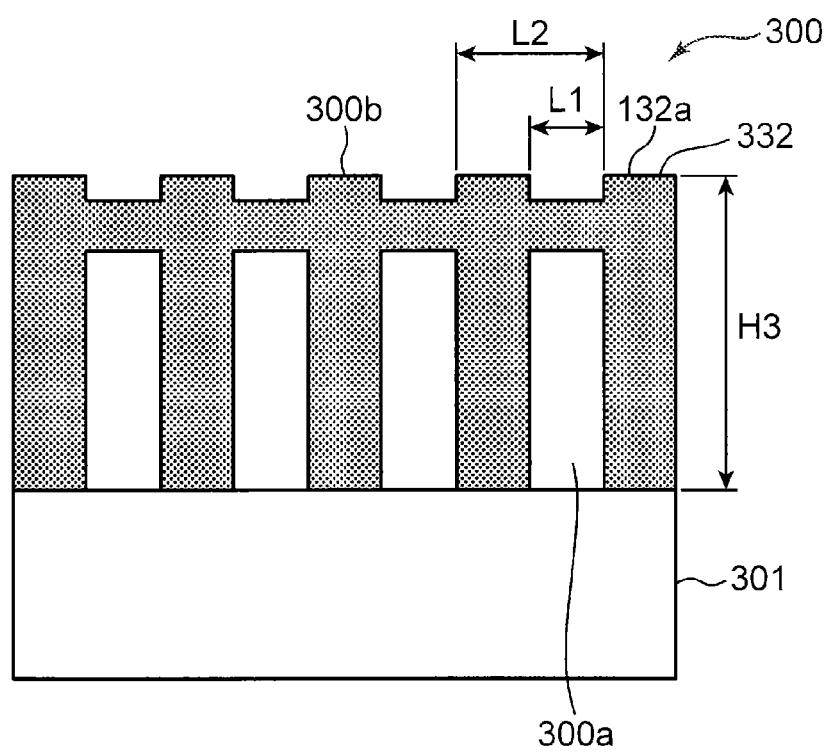
FIG. 22 is a cross-sectional view of a mold for manufacturing an ultrasonic probe of an eighth embodiment as one example manufactured by the method for manufacturing the high aspect ratio structure.
Figure 23:
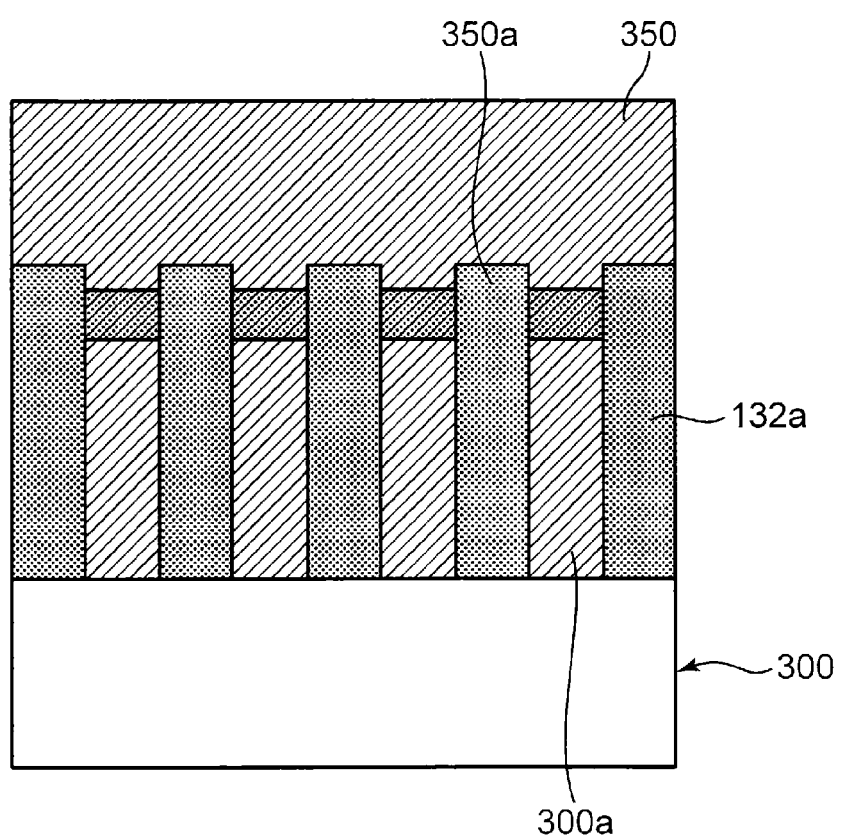
FIG. 23 is a cross-sectional view when a metal mold is formed, using the mold for manufacturing the ultrasonic probe.
Figure 24:
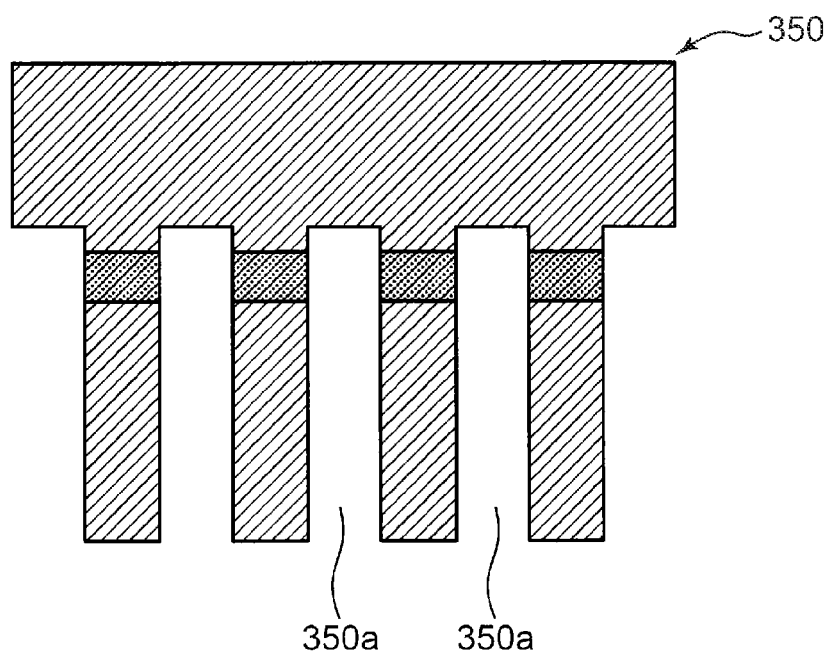
FIG. 24 is a cross-sectional view of the metal mold shown in FIG. 23.
Figure 25:
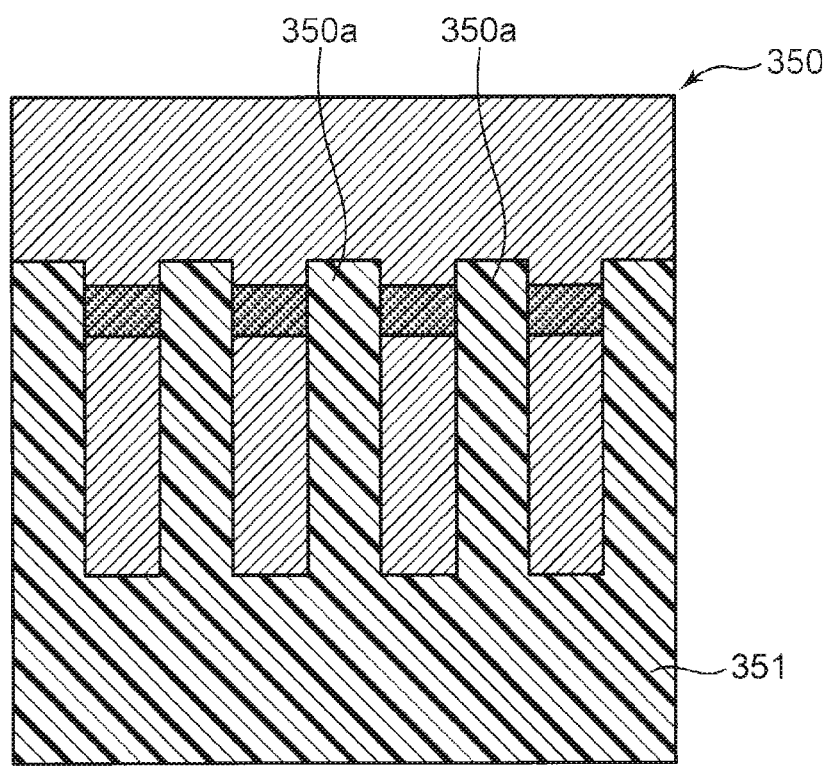
FIG. 25 is a cross-sectional view when a resin mold is formed, using the metal mold in FIG. 23.
Figure 26:
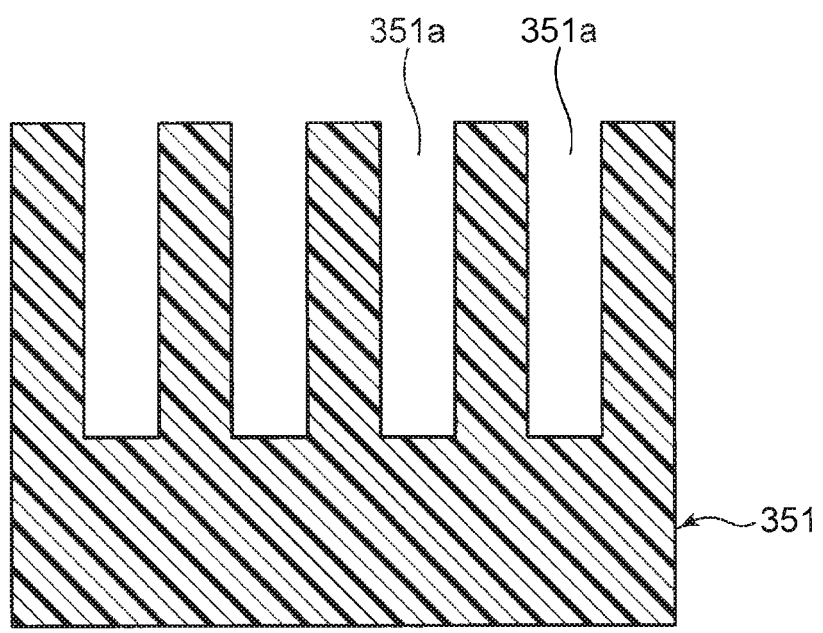
FIG. 26 is a cross-sectional view of the resin mold in FIG. 25.
Figure 27:
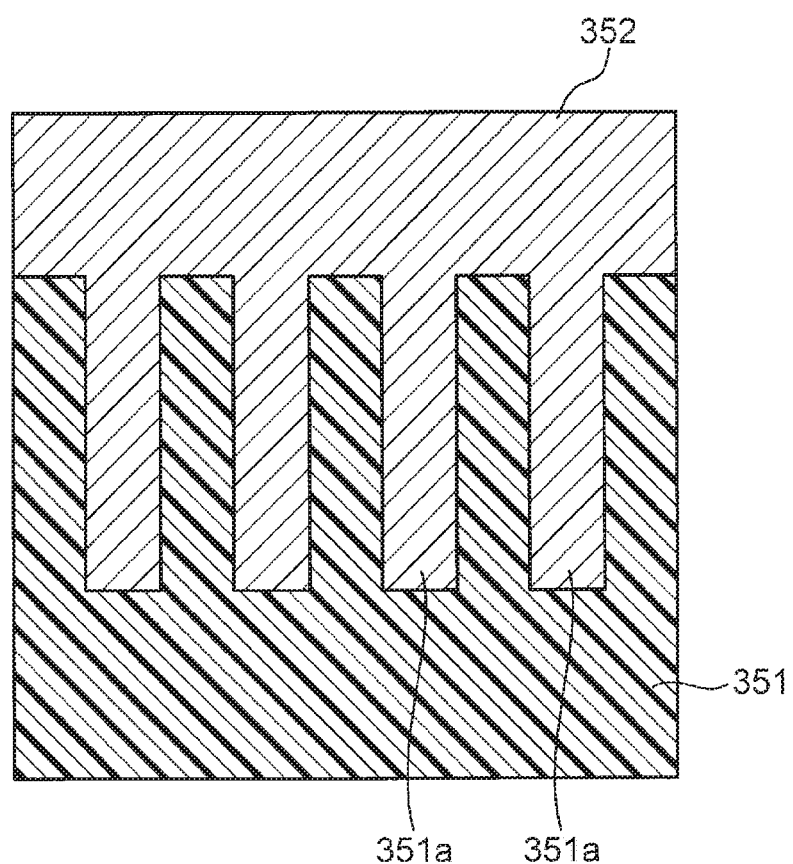
FIG. 27 is a cross-sectional view when a lead zirconium titanate sintered body is formed, using the resin mold in FIG. 26.
Figure 28:
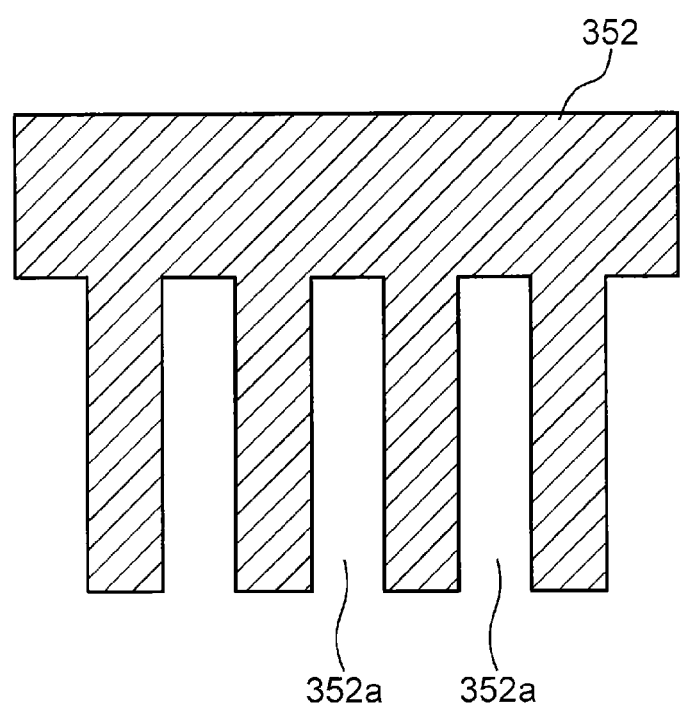
FIG. 28 is a cross-sectional view of the lead zirconium titanate sintered body in FIG. 27.
Figure 29:
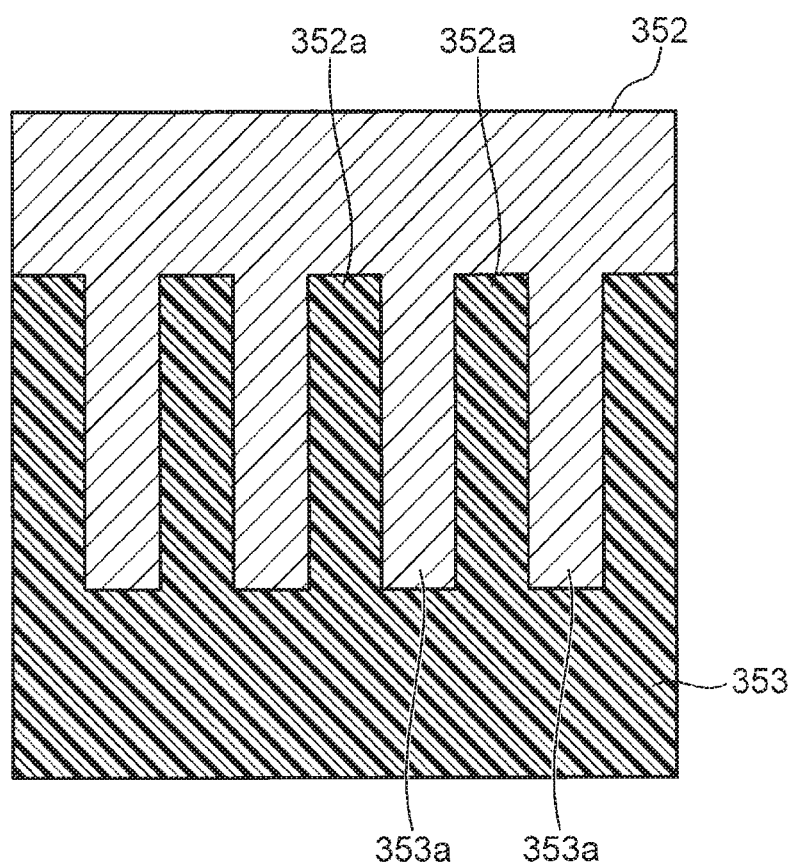
FIG. 29 is a cross-sectional view when sintered body recesses are filled with epoxy resin, the sintered body recesses being provided in the lead zirconium titanate sintered body in FIG. 28.
Figure 30:
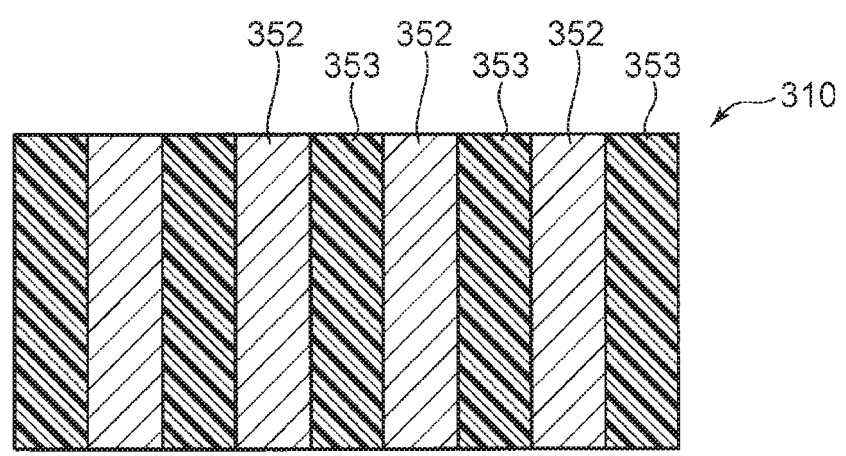
FIG. 30 is a cross-sectional view of a substantial portion of the ultrasonic probe formed from a state in FIG. 29.

FIG. 22 is a cross-sectional view of a mold for manufacturing an ultrasonic probe of an eighth embodiment as one example manufactured by the method for manufacturing the high aspect ratio structure. FIG. 23 is a cross-sectional view when a metal mold is formed, using the mold for manufacturing the ultrasonic probe. FIG. 24 is a cross-sectional view of the mold shown in FIG. 23. FIG. 25 is a cross-sectional view when a resin mold is formed, using the metal mold in FIG. 23. FIG. 26 is a cross-sectional view of the resin mold in FIG. 25. FIG. 27 is a cross-sectional view when a lead zirconium titanate sintered body is formed, using the resin mold in FIG. 26. FIG. 28 is a cross-sectional view of the lead zirconium titanate sintered body in FIG. 27. FIG. 29 is a cross-sectional view when sintered body recesses are filled with epoxy resin, the sintered body recesses being provided in the lead zirconium titanate sintered body in FIG. 28. FIG. 30 is a cross-sectional view of a substantial portion of the ultrasonic probe formed from a state in FIG. 29.

In one example, by respective steps similar to the case where the metal grating for X-ray 1b of the second embodiment is manufactured, as shown in FIG. 22, in a main surface of a substrate 301 made of aluminum, there is produced a mold for manufacturing an ultrasonic probe 300 as a high aspect ratio structure having a one-dimensional structure, in which a plurality of recesses 300a having a width L1 of 15 um and a depth H3 of 100 um, and a plurality of projections 300b having a width of 15 um and the depth H3 of 100 um are alternately arranged at a pitch interval L2 of 30 um (=a period 30 um). While in this example, the mold for manufacturing the ultrasonic probe 300 is produced by the respective steps similar to those in the case where the metal grating for X-ray 1b of the second embodiment is formed, the mold for manufacturing the ultrasonic probe 300 may be produced by the respective steps similar to those in the case where the metal gratings for X-ray 1a, 1c in the first and third embodiments are formed.

Next, as shown in FIG. 23, electroforming is carried out, in which the substrate 301 of bottom portions of the recesses 300a in this mold for manufacturing the ultrasonic probe 300 serves as a plating electrode, and the recesses 300a are filled with a nickel filler made of nickel, and the nickel filler is deposited until a thickness thereof becomes 1 mm. Thereafter, the mold for manufacturing the ultrasonic probe 300 is dissolved and removed with phosphoric acid liquid, and as shown in FIG. 24, a metal mold 350 having recesses for metal mold 350a are produced (a metal mold formation step).

Next, as shown in FIG. 25, this produced metal mold 350 is filled with a resin filler made of a resin material. The resin material is, for example, acrylic resin made of polymethylmethacrylate (PMMA). Syrupy acrylic resin softened by heating is poured into the recesses for metal mold 350a of the metal mold 350, and is cooled to a room temperature to thereby be hardened. Thereafter, the resin material is released from the metal mold 350, and as shown in FIG. 26, a resin mold 351 having recesses for resin mold 351a is produced (a resin mold formation step).

Next, as shown in FIG. 27, the recesses for resin mold 351a of the resin mold 351 is filled with slurry containing lead zirconate titanate (PZT) particles. This slurry is prepared, using water and an organic binder. Next, the charged slurry is solidified by drying. Thereafter, ashing using oxygen plasma is carried out to remove the resin mold 351 (FIG. 28). Next, the solidified material of the left slurry is preliminarily fired at 500° C., and further finally fired at 1100° C. By this firing, as shown in FIG. 28, there is produced a lead zirconate titanate (PZT) sintered body 352 as a piezoelectric material configured by a minute structure having sintered body recesses (structure recesses) 352a (a minute structure formation step).

The sintered body recesses 352a of the lead zirconium titanate sintered body 352 produced in this manner are filled with epoxy resin 353, as shown in FIG. 29, and then, a base portion of the epoxy resin 353 and the lead zirconium titanate sintered body 352 is removed by polishing as shown in FIG. 30. This allows an ultrasonic probe body 310 to be formed, the ultrasonic probe body 310 having the lead zirconium titanate sintered body 352 and the epoxy resin 353 arrayed alternately side by side (an ultrasonic probe body formation step). Thereafter, electrodes are formed in both surfaces of the ultrasonic probe body 310, by which the ultrasonic probe is produced.

As described above, in the mold for manufacturing the ultrasonic probe 300 as the high aspect ratio structure, which mold is used in the method for manufacturing the ultrasonic probe, the plurality of recesses 300a formed in the one main surface of the substrate 301 by wet etching each have side surfaces perpendicular to the main surface of the substrate 301. In the method for manufacturing this ultrasonic probe, by manufacturing the ultrasonic probe 310 on the basis of this mold for manufacturing the ultrasonic probe 300, the lead zirconium titanate sintered body 352 and the epoxy resin 353 can be accurately arrayed alternately side by side, and additionally, the ultrasonic probe 310 can be manufactured at a low cost.

The specification discloses the aforementioned arrangements. The following is a summary of the primary arrangements of the embodiments.

A method for manufacturing a high aspect ratio structure according to one aspect includes a hole formation step of forming the plurality of holes extending in the direction crossing the main surface in at least the one main surface of the predetermined substrate, a region definition step of periodically defining, in the main surface where the plurality of holes are formed, the plurality of first regions, and the plurality of second regions excluding the plurality of first regions from the main surface, and a partition-wall partially leaving/removing step of immersing the substrate in the etching liquid and thereby removing the partition walls between the plurality of holes formed in the substrate corresponding to the first regions so that part of the partition walls within the predetermined range along the direction, excluding the bottom portions of the plurality of holes are left, wherein the hole formation step includes a partition-wall thinning hole formation step of forming the plurality of holes so that a partition wall thickness between the holes adjacent to each other becomes smaller on the bottom side of the holes than that on the main surface side. Preferably, in the foregoing method for manufacturing the high aspect ratio structure, the hole formation step is configured by the partition-wall thinning hole formation step itself. Preferably, in the foregoing method for manufacturing the high aspect ratio structure, the predetermined range is a range from the main surface to a predetermined first length along the direction. Preferably, in the foregoing method for manufacturing the high aspect ratio structure, the predetermined range is a range from a position at a distance of a predetermined second length from the main surface along the direction to a predetermined third length along the direction (the predetermined range is a range located in the middle of a section from the main surface to the bottom portion of each of the plurality of holes). Preferably, in the foregoing method for manufacturing the high aspect ratio structure, the predetermined range is a range located in a center of the section from the main surface to the bottom portion of each of the plurality of holes. Preferably, in the foregoing method for manufacturing the high aspect ratio structure, the predetermined range is a range located closer to the main surface than a central position in the section from the main surface to the bottom portion of each of the plurality of holes.

Since the above-described method for manufacturing the high aspect ratio structure includes the partition-wall partially leaving/removing step of immersing the metal substrate in the etching liquid, and thereby removing the partition walls between the plurality of holes formed in the substrate corresponding to the first regions so as to leave the part of the partition walls within the predetermined range along the direction, excluding the bottom portions of the plurality of holes, the substrate are supported by porous members left within the predetermined range and each including the plurality of holes, so that even if the substrate corresponding to the first regions are subjected to the etching, occurrence of sticking can be reduced more. In addition, since the above-described method for manufacturing the high aspect ratio structure includes the partition-wall thinning hole formation step of forming the plurality holes so that the partition wall thickness between the holes adjacent to each other becomes smaller on the bottom side of the holes than that on the main surface side, the partition walls on the bottom surface side having the relatively smaller partition wall thickness can be removed dominantly with the lapse of etching time when the wet etching method is carried out, and when the partition walls on the bottom surface side are dissolved and removed, the partition walls on the surface side having the relatively larger partition wall thickness can be left, in the partition-wall partially leaving/removing step, the part of the partition walls can be easily left within the predetermined range along the direction, excluding the bottom portions of the plurality of holes.

An aspect ratio is a ratio of a thickness (a depth) to a width of each recess (the aspect ratio=the thickness/the width=the depth/the width). The high aspect ratio indicates a case where the aspect ratio is three or more.

According to another aspect, in the foregoing method for manufacturing the high aspect ratio structure, the hole formation step includes a first hole formation step carried out before the region definition step is carried out, and a second hole formation step carried out after the region definition step is carried out, and the second hole formation step is the partition-wall thinning hole formation step of further forming a plurality of holes so as to further extend in the direction continuously to the respective plurality of holes formed in the first hole formation step. Preferably, in the foregoing method for manufacturing the high aspect ratio structure, in the first hole formation step, the plurality of holes are formed by an anodic oxidation method or an anodization method carried out at an applied voltage of a constant value from the start time to the end time.

According to another aspect, in the foregoing method for manufacturing the high aspect ratio structure, the first hole formation step is the partition-wall thinning hole formation step.

According to another aspect, in the foregoing method for manufacturing the high aspect ratio structure, the hole formation step includes a first hole formation step carried out before the region definition step is carried out, and a second hole formation step carried out after the region definition step is carried out, the first hole formation step is the partition-wall thinning hole formation step, and in the second hole formation, a plurality of holes are further formed so as to further extend in the direction continuously to the respective plurality of holes formed in the first hole formation step. Preferably, in the foregoing method for manufacturing the high aspect ratio structure, in the second hole formation step, the plurality of holes are formed by an anodic oxidation method or an anodization method carried out at an applied voltage of a constant value from the start time to the end time.

In the foregoing methods for manufacturing the high aspect ratio structure, since the hole formation step is divided into the first and second hole formation steps, in base portions of the projections formed between the recesses adjacent to each other in the partition-wall partially leaving/removing step, the plurality of holes are not formed, the projections can be more firmly supported.

According to another aspect, in the foregoing methods for manufacturing the high aspect ratio structure, the region definition step is a resist layer formation step of forming a resist layer on the main surface corresponding to the second regions.

In the above-described method for manufacturing the high aspect ratio structure, by forming the resist layer on the main surface corresponding to the second regions, the second regions, where the partition walls are not removed in the partition-wall partially leaving/removing step, can be defined (formed), and the region definition step can be easily implemented in the resist layer formation step.

According to another aspect, in the foregoing methods for manufacturing the high aspect ratio structure, the region definition step is a closing step of closing one or a plurality of holes formed in portions corresponding to the second regions of the plurality of holes. Preferably, in the foregoing method for manufacturing the high aspect ratio structure, the closing step includes a first step of forming a second resist layer on the main surface, a second step of patterning the second resist layer to remove the second resist layer corresponding to the second regions, a third step of closing the one or the plurality of holes in each of the second regions with the second resist layer removed in the second step of the plurality of holes, and a fourth step of removing the second resist layer left after the second step. Preferably, in the foregoing method for manufacturing the high aspect ratio structure, the closing step is a step of closing the holes by hole-sealing treatment using a hole-sealing material.

In the above-described method for manufacturing the high aspect ratio structure, by closing the one or the plurality of holes formed in the portion corresponding to each of the second regions of the plurality of holes, the second regions where the partition walls are not removed in the partition-wall partially leaving/removing step can be defined (formed), and the region definition step can be easily implemented in the closing step. In the above-described method for manufacturing the high aspect ratio structure, since the closing step prevents the etching liquid from entering the holes when the wet etching method is carried out, the resist layer against the etching liquid, which is normally required when the wet etching method is carried out, becomes unnecessary. Therefore, in the above-described method for manufacturing the high aspect ratio structure, so-called undercut by the resist layer, which normally occurs when the wet etching method is carried out, does not occur, and the etching liquid permeates to the bottom portions of the holes to dissolve the partition walls formed between the holes adjacent to each other. Accordingly, in the above-described method for manufacturing the high aspect ratio structure, the high aspect ratio structure having the recesses each having side surfaces substantially perpendicular to the main surface of the substrate can be manufactured by the wet etching method.

According to another aspect, in the foregoing methods for manufacturing the high aspect ratio structure, the partition-wall thinning hole formation step is a step of forming the plurality of holes by the anodic oxidation method or the anodization method carried out so that a second applied voltage at the end time becomes lower than a first applied voltage at the start time. Preferably, in the foregoing method for manufacturing the high aspect ratio structure, the anodic oxidation method or the anodization method in the partition-wall thinning hole formation step is carried out at an applied voltage gradually decreasing with the lapse of time. Preferably, in the foregoing method for manufacturing the high aspect ratio structure, the anodic oxidation method or the anodization method in the partition-wall thinning hole formation step is carried out at an applied voltage decreasing at a predetermined ratio with the lapse of time. Preferably, the predetermined ratio is a predetermined constant value regardless of the lapse of time (the anodic oxidation method or the anodization method in the partition-wall thinning hole formation step is carried out at the applied voltage changing and decreasing linearly with a predetermined inclination with the lapse of time. The anodic oxidation method or the anodization method in the partition-wall thinning hole formation step is carried out at the applied voltage decreasing at a predetermined constant value per unit time). Preferably, the predetermined ratio is a value changing with the lapse of time (The predetermined inclination is a value changing with the lapse of time. The anodic oxidation method or the anodization method in the partition-wall thinning hole formation step is carried out at the applied voltage changing and decreasing nonlinearly with the lapse of time).

In the above-described method for manufacturing the high aspect ratio structure, since in the partition-wall thinning hole formation step, the anodic oxidation method or the anodization method is used, and the applied voltage in the anodic oxidation method or the anodization method is adjusted so that the second applied voltage at the end time becomes lower than the first applied voltage at the start time, the plurality of holes can be formed on the main surface of the substrate, in which the partition wall thickness between the holes adjacent to each other becomes smaller on the bottom side of the holes than that on the main surface side.

According to another aspect, in the foregoing methods for manufacturing the high aspect ratio structure, the predetermined substrate is formed of any one of aluminum (Al), tungsten (W), molybdenum (Mo), silicon (Si), gallium arsenide (GaAs), and indium phosphide (InP).

In the above-described method for manufacturing the high aspect ratio structure, since the substrate is formed of any one of these, the plurality of holes extending substantially perpendicularly to the main surface can be easily formed, for example, by the anodic oxidation method or the anodization method.

According to another aspect, the foregoing methods for manufacturing the high aspect ratio structure further include an X-ray absorbent material burying step of burying an X-ray absorbent material capable of absorbing X-rays in the recesses.

In the above-described method for manufacturing the high aspect ratio structure, burying the X-ray absorbent material in the recesses enables the first regions to be formed as the X-ray absorption portions, and the second regions to be formed as the X-ray transmission portions.

According to another aspect, in the foregoing methods for manufacturing the high aspect ratio structure, in the X-ray absorbent material burying step, a metal as the X-ray absorbent material is buried by electroforming. Preferably, in the foregoing method for manufacturing the high aspect ratio structure, the metal is any one of gold (Au), platinum (Pt), rhodium (Rh), ruthenium (Ru), and iridium (Ir).

In the above-described method for manufacturing the high aspect ratio structure, the metal as the X-ray absorbent material is buried by electroforming, which enables the X-ray absorbent material to be easily and surely buried in the recesses.

According to another aspect, in the foregoing methods for manufacturing the high aspect ratio structure, the high aspect ratio structure is a metal grating for X-ray used in an X-ray Talbot interferometer or an X-ray Talbot-Lau interferometer.

The above-described method for manufacturing the high aspect ratio structure can manufacture higher-performance metal gratings for X-ray of a 0-th grating, a first grating, and a second grating used in the X-ray Talbot interferometer or the X-ray Talbot-Lau interferometer.

According to another aspect, in the foregoing methods for manufacturing the high aspect ratio structure, the high aspect ratio structure is a mold for manufacturing an ultrasonic probe used when the ultrasonic probe is manufactured.

In the above-described method for manufacturing the high aspect ratio structure, the mold for manufacturing the ultrasonic probe used when the ultrasonic probe is manufactured can be easily manufactured at a low cost.

A method for manufacturing an ultrasonic probe according to another aspect includes a metal mold formation step of filling recesses of the foregoing mold for manufacturing an ultrasonic probe with a metal to form a metal mold having recesses for metal mold, a resin mold formation step of filling the recesses for metal mold of the metal mold with a resin filler made of a resin material to form a resin mold having recesses for resin mold, a minute structure formation step of filling the recesses for resin mold of the resin mold with a slurry containing a piezoelectric material to form a minute structure having structure recesses, and an ultrasonic probe body formation step of filling the structure recesses of the minute structure with a synthetic resin to form an ultrasonic probe body in which a piezoelectric layer made of the piezoelectric material, and a synthetic resin layer made of the synthetic resin are arrayed alternately side by side.

In the above-described method for manufacturing the ultrasonic probe, the ultrasonic probe body can be formed, in which the piezoelectric layer and the synthetic resin layer are accurately arrayed alternately side by side on the basis of the mold for manufacturing the ultrasonic probe with occurrence of the sticking reduced more even by the wet etching method, and in addition, it can be manufactured at a low cost.

A high aspect ratio structure according to another aspect includes a substrate, and a grating formed in the substrate, wherein the grating includes a plurality of projections formed so as to have a spatial period, each of the plurality of projections includes a plurality of holes extending in a direction crossing a grating surface of the grating, a thickness of partition walls between the holes adjacent to each other in each of the plurality of projections becomes smaller on the bottom side of the holes than that on the grating surface side, and a plurality of recesses formed between the plurality of projections each includes, over side walls, a porous member including a plurality of holes extending in the direction crossing the grating surface within a predetermined range excluding a bottom portion, the predetermined range being a section inside each of the recesses and from the grating surface to the bottom portion of the relevant recess. Preferably, in the foregoing high aspect ratio structure, the predetermined range is a range from the grating surface to a predetermined first length along the direction. Preferably, in the foregoing high aspect ratio structure, the predetermined range is a range from a position at a distance of a predetermined second length from the grating surface along the direction to a predetermined third length along the direction (the predetermined range is a range located in the middle of the section from the grating surface to the bottom portion of each of the recesses). Preferably, in the foregoing high aspect ratio structure, the predetermined range is a range located in a center from the grating surface to the bottom portion of each of the recesses. Preferably, in the foregoing high aspect ratio structure, the predetermined range is a range located closer to the grating surface than a central position in the section from the grating surface to the bottom portion of each of the recesses.

Since the above-described high aspect ratio structure can be manufactured by any of the foregoing methods for manufacturing the high aspect ratio structure, even when the wet etching method is utilized during the manufacturing step, the sticking can be reduced more, and manufacturing yield becomes higher.

According to another one aspect, in the foregoing high aspect ratio structure, each of the plurality of projections further includes a closing member configured to close each of the plurality holes. Preferably, in the foregoing high aspect ratio structure, the substrate is formed of aluminum, the projections are formed of aluminum oxide (alumina), and the closing member is formed a hydrate of aluminum oxide (alumina).

Since the above-described high aspect ratio structure includes the closing member, even when the wet etching method is utilized during the manufacturing step, undercut by the foregoing resist layer does not occur, so that the recesses each have side surfaces substantially perpendicular to the main surface of the substrate. Accordingly, the high aspect ratio structure is more elaborate. Additionally, the high aspect ratio structure can be manufactured at a low cost.

According to another aspect, the foregoing high aspect ratio structures further each include a plurality of X-ray absorption members buried in the respective plurality of recesses formed between the respective plurality of projections, and made of an X-ray absorbent material capable of absorbing X-rays.

The above-described high aspect ratio structure is the metal grating for X-ray in which the first regions are X-ray absorption portions and the second regions are X-ray transmission portions.

An X-ray imaging apparatus according to another aspect includes an X-ray source configured to radiate X-rays, a Talbot interferometer or a Talbot-Lau interferometer configured to be irradiated with the X-rays radiated from the X-ray source, and an X-ray imaging element configured to capture an image of the X-rays by the Talbot interferometer or the Talbot-Lau interferometer, wherein the Talbot interferometer or the Talbot-Lau interferometer includes any of the foregoing high aspect ratio structures as a metal grating for X-ray.

Since the above-described X-ray imaging apparatus uses the foregoing higher-performance, high aspect ratio structure for the metal grating for X-ray configuring the Talbot interferometer or the Talbot-Lau interferometer, a clearer image can be obtained.

Japanese Patent Application No. 2017-46372 filed on Mar. 10, 2017, including description, claims, drawings, and abstract, the entire disclosure is incorporated herein by reference in its entirety.

Although embodiments of the present invention have been described and illustrated in detail, it is clearly understood that the same is by way of illustration and example only and not limitation, the scope of the present invention should be interpreted by terms of the appended claims.

While in order to represent the present invention, the present invention has been properly and sufficiently described through the embodiments with reference to the drawings in the foregoing, a person skilled in the art should recognize that modifications and/or improvements can be easily made to the foregoing embodiments. Accordingly, it is construed that unless a modified form and an improved form carried out by a person skilled in the art is at a level that departs from the scope of the right of the claims, the relevant modified form or the relevant improved form is included in the scope of the right of the claims.

The invention claimed is:

1. A method for manufacturing a high aspect ratio structure, the method comprising:
   a hole formation step of forming a plurality of holes extending in a direction crossing a main surface in at least the one main surface of a predetermined substrate;
   a region definition step of periodically defining, in the main surface where the plurality of holes are formed, a plurality of first regions and a plurality of second regions excluding the plurality of first regions from the main surface; and
   a partition-wall partially leaving/removing step of immersing the substrate in an etching liquid and thereby removing partition walls between the plurality of holes formed in the substrate corresponding to the first regions so that part of the partition walls within a predetermined range along the direction excluding bottom portions of the plurality of holes are left,
   wherein the hole formation step includes a partition-wall thinning hole formation step of forming the plurality of holes so that a partition wall thickness between the holes adjacent to each other becomes smaller on the bottom side of the holes than that on the main surface side.

2. The method for manufacturing the high aspect ratio structure according to claim 1,
   wherein
   the hole formation step comprises a first hole formation step carried out before the region definition step is carried out, and a second hole formation step carried out after the region definition step is carried out, and
   the second hole formation step is the partition-wall thinning hole formation step of further forming a plurality of holes so as to further extend in the direction continuously to the respective plurality of holes formed in the first hole formation step.

3. The method for manufacturing the high aspect ratio structure according to claim 2, wherein the first hole formation step is the partition-wall thinning hole formation step.

4. The method for manufacturing the high aspect ratio structure according to claim 1,
   wherein
   the hole formation step comprises a first hole formation step carried out before the region definition step is carried out, and a second hole formation step carried out after the region definition step is carried out,
   the first hole formation step is the partition-wall thinning hole formation step, and
   in the second hole formation step, a plurality of holes are further formed so as to further extend in the direction continuously to the respective plurality of holes formed in the first hole formation step.

5. The method for manufacturing the high aspect ratio structure according to claim 1, wherein the region definition step is a resist layer formation step of forming a resist layer in the main surface corresponding to the second regions.

6. The method for manufacturing the high aspect ratio structure according to claim 1, wherein the region definition step is a closing step of closing one or a plurality of holes formed in portions corresponding to the second regions of the plurality of holes.

7. The method for manufacturing the high aspect ratio structure according to claim 1, wherein the partition-wall thinning hole formation step is a step of forming the plurality of holes by an anodic oxidation method or an anodization method carried out so that a second applied voltage at the end time becomes lower than a first applied voltage at the start time.

8. The method for manufacturing the high aspect ratio structure according to claim 1, wherein the predetermined substrate is formed of any one of aluminum (Al), tungsten (W), molybdenum (Mo), silicon (Si), gallium arsenide (GaAs), and indium phosphide (InP).

9. The method for manufacturing the high aspect ratio structure according to claim 1, the method further comprising an X-ray absorbent material burying step of burying an X-ray absorbent material capable of absorbing X-rays in the recesses.

10. The method for manufacturing the high aspect ratio structure according to claim 9, wherein in the X-ray absorbent material burying step, a metal as the X-ray absorbent material is buried by electroforming.

11. The method for manufacturing the high aspect ratio structure according to claim 1, wherein the high aspect ratio structure is a metal grating for X-ray used in an X-ray Talbot interferometer or an X-ray Talbot-Lau interferometer.

12. The method for manufacturing the high aspect ratio structure according to claim 1, wherein the high aspect ratio structure is a mold for manufacturing an ultrasonic probe used when the ultrasonic probe is manufactured.

13. A method for manufacturing an ultrasonic probe comprising:
   a metal mold formation step of filling recesses of the mold for manufacturing the ultrasonic probe according to claim 12 with a metal to form a metal mold having recesses for metal mold;
   a resin mold formation step of filling the recesses for metal mold of the metal mold with a resin filler made of a resin material to form a resin mold having recesses for resin mold;
   a minute structure formation step of filling the recesses for resin mold of the resin mold with a slurry containing a piezoelectric material to form a minute structure having structure recesses; and
   an ultrasonic probe body formation step of filling the structure recesses of the minute structure with a synthetic resin to form an ultrasonic probe body in which a piezoelectric layer made of the piezoelectric material, and a synthetic resin layer made of the synthetic resin are arrayed alternately side by side.

14. A high aspect ratio structure comprising:
   a substrate; and
   a grating formed in the substrate,
   wherein
   the grating includes a plurality of projections formed so as to have a spatial period,
   each of the plurality of projections includes a plurality of holes extending in a direction crossing a grating surface of the grating,
   a thickness of partition walls between the holes adjacent to each other in each of the plurality of projections becomes smaller on the bottom side of the holes than that on the grating surface side, and
   a plurality of recesses formed between the plurality of projections each include, over a side wall, a porous member including a plurality of holes extending in the direction crossing the grating surface within a predetermined range excluding a bottom portion, the predetermined range being a section inside each of the recesses and from the grating surface to the bottom portion of the relevant recess.

15. The high aspect ratio structure according to claim 14, wherein each of the plurality of projections further comprises a closing member configured to close each of the plurality holes.

16. The high aspect ratio structure according to claim 14, further comprising a plurality of X-ray absorption members buried in the respective plurality of recesses, and made of an X-ray absorbent material capable of absorbing X-rays.

17. An X-ray imaging apparatus comprising:
an X-ray source configured to radiate X-rays;
a Talbot interferometer or a Talbot-Lau interferometer configured to be irradiated with the X-rays radiated from the X-ray source; and
an X-ray imaging element configured to capture an image of the X-rays by the Talbot interferometer or the Talbot-Lau interferometer,
wherein the Talbot interferometer or the Talbot-Lau interferometer includes the high aspect ratio structure according to claim 14 as a metal grating for X-ray.

* * * * *